United States Patent
MacMahon et al.

(10) Patent No.: US 11,058,540 B2
(45) Date of Patent: Jul. 13, 2021

(54) ATRAUMATIC ADJUSTMENT OR REPLACEMENT OF A DEVICE FOR TREATING VALVE REGURGITATION

(71) Applicant: Mitre Medical Corp., Morgan Hill, CA (US)

(72) Inventors: John MacMahon, Exeter, NH (US); Evan Anderson, Woodside, CA (US); Jeremy Boyette, Menlo Park, CA (US)

(73) Assignee: Mitre Medical Corp., Morgan Hill, CA (US)

( * ) Notice: Subject to any disclaimer, the term of this patent is extended or adjusted under 35 U.S.C. 154(b) by 342 days.

(21) Appl. No.: 16/258,525

(22) Filed: Jan. 25, 2019

(65) Prior Publication Data
US 2019/0231528 A1 Aug. 1, 2019

Related U.S. Application Data

(60) Provisional application No. 62/622,831, filed on Jan. 27, 2018, provisional application No. 62/622,830, (Continued)

(51) Int. Cl.
*A61F 2/24* (2006.01)
*A61B 17/10* (2006.01)
(Continued)

(52) U.S. Cl.
CPC .......... *A61F 2/2481* (2013.01); *A61B 17/068* (2013.01); *A61B 17/10* (2013.01);
(Continued)

(58) Field of Classification Search
CPC ........ A61F 2/00; A61F 2/2442; A61F 2/2451; A61F 2/2478; A61F 2/81
See application file for complete search history.

(56) References Cited

U.S. PATENT DOCUMENTS

| 4,042,979 A | 8/1977 | Angell |
| 6,908,482 B2 | 6/2005 | McCarthy et al. |

(Continued)

FOREIGN PATENT DOCUMENTS

WO WO2004043265 5/2004

OTHER PUBLICATIONS

Grayburn et al., "Proportionate and Disproportionate Functional Mitral Regurgitation", JACC Cardiovascular Imaging, 2018, pp. 1-10.
(Continued)

*Primary Examiner* — John P Lacyk
(74) *Attorney, Agent, or Firm* — Law Office of Alan W. Cannon

(57) ABSTRACT

An epicardial device for reducing or preventing regurgitation of blood through a valve of a heart includes a main body having a segment adapted to apply force to an epicardial surface of the heart. A member that applies counterforce to the force applied by the segment is also provided. A foundation is configured to be anchored to the epicardial surface of the heart. The foundation includes a surface configured with attachment features. The device further includes a surface configured with mating attachment features configured to attach to the attachment features of the foundation. The mating attachment features and attachment features are separable and reattachable to allow repositioning of at least a portion of the device relative to the foundation.

34 Claims, 21 Drawing Sheets

Related U.S. Application Data filed on Jan. 27, 2018, provisional application No. 62/622,827, filed on Jan. 27, 2018.

(51) Int. Cl.

| | | |
|---|---|---|
| *A61B 90/00* | (2016.01) | |
| *A61B 17/068* | (2006.01) | |
| *A61B 17/00* | (2006.01) | |
| *A61B 17/28* | (2006.01) | |
| *A61B 17/064* | (2006.01) | |

(52) U.S. Cl.
CPC .............. *A61B 90/06* (2016.02); *A61F 2/246* (2013.01); *A61F 2/2442* (2013.01); *A61F 2/2451* (2013.01); *A61F 2/2466* (2013.01); *A61F 2/2478* (2013.01); *A61B 17/064* (2013.01); *A61B 17/2812* (2013.01); *A61B 2017/00243* (2013.01); *A61B 2017/00398* (2013.01); *A61B 2017/00407* (2013.01); *A61B 2017/00473* (2013.01); *A61B 2017/00738* (2013.01); *A61B 2017/00858* (2013.01); *A61B 2017/0649* (2013.01); *A61B 2090/061* (2016.02); *A61B 2090/0801* (2016.02); *A61F 2002/2484* (2013.01); *A61F 2210/0033* (2013.01); *A61F 2210/0076* (2013.01); *A61F 2220/0016* (2013.01); *A61F 2220/0025* (2013.01); *A61F 2220/0033* (2013.01); *A61F 2220/0083* (2013.01); *A61F 2230/0013* (2013.01); *A61F 2230/0023* (2013.01); *A61F 2250/001* (2013.01); *A61F 2250/0002* (2013.01); *A61F 2250/0003* (2013.01); *A61F 2250/0004* (2013.01); *A61F 2250/006* (2013.01); *A61F 2250/0007* (2013.01); *A61F 2250/0029* (2013.01); *A61F 2250/0036* (2013.01); *A61F 2250/0064* (2013.01)

(56) References Cited

U.S. PATENT DOCUMENTS

| | | |
|---|---|---|
| 7,591,826 B2 | 9/2009 | Alferness et al. |
| 7,766,812 B2 | 8/2010 | Schroeder et al. |
| 8,012,202 B2 | 9/2011 | Alameddine |
| 8,262,725 B2 | 9/2012 | Subramanian |
| 8,647,254 B2 | 2/2014 | Callas et al. |
| 8,956,407 B2 | 2/2015 | Macoviak et al. |
| 9,566,443 B2 | 2/2017 | de Canniere |
| 9,615,926 B2 | 4/2017 | Lashinski et al. |
| 9,636,223 B2 | 5/2017 | Khalil et al. |
| 9,724,194 B2 | 8/2017 | Callas et al. |
| 9,795,481 B2 | 10/2017 | Callas et al. |
| 2002/0111533 A1 | 8/2002 | Melvin |
| 2004/0064014 A1 | 4/2004 | Melvin et al. |
| 2005/0119735 A1 | 6/2005 | Spence et al. |
| 2007/0066863 A1 | 3/2007 | Rafiee et al. |
| 2010/0004504 A1 | 1/2010 | Callas et al. |
| 2010/0010538 A1 | 1/2010 | Juravic et al. |
| 2012/0323314 A1 | 12/2012 | Callas et al. |
| 2013/0030522 A1 | 1/2013 | Rowe et al. |
| 2014/0172084 A1 | 6/2014 | Callas et al. |
| 2015/0366556 A1 | 12/2015 | Khairkhahan et al. |
| 2018/0008412 A1 | 1/2018 | Callas et al. |

OTHER PUBLICATIONS

Kashem et al., "CardioClasp: A New Passive Device to Re-Shape Cardiac Enlargement", ASAIO Journal, 2002, pp. 1-7.

Tibayan et al., "Does septal-lateral annular cinching work for chronic ischemic mitral regurgitation?", The Journal of Thoracic and Cardiovascular Surgery, Mar. 2004, pp. 654-663.

Fattouch et al., "Mitral valve therapy still surgical?", European Heart Journal Supplements, Mar. 2015, pp. A43-A48.

ATRAUMATIC ADJUSTMENT OR REPLACEMENT OF A DEVICE FOR TREATING VALVE REGURGITATION

CROSS-REFERENCE

This application claims the benefit of U.S. Provisional application Ser. Nos. 62/622,831, filed Jan. 27, 2018; 62/622,830, filed Jan. 27, 2018; and 62/622,827, filed Jan. 27, 2018, each of which applications is hereby incorporated herein, in its entirety, by reference thereto.

INCORPORATION BY REFERENCE

All publications and patent applications mentioned in this specification are herein incorporated by reference to the same extent as if each individual publication or patent application was specifically and individually indicated to be incorporated by reference. This specification specifically incorporates US Patent Application Publication Nos. 2010/0004504 A1 and 2012/0323314 A1 herein, in their entireties, by reference thereto. Also specifically incorporated by reference in their entireties, are U.S. Provisional Application Ser. Nos. 62/622,831, 62/622,827; and 62/622,830, as noted above. Further, this specification specifically incorporates in its entirety International Application Serial No. PCT/US2019/015300, titled "Epicardial Valve Repair System", filed concurrently herewith; International Application Serial No. PCT/US2019/015302, titled "Self-Adjusting Device", filed concurrently herewith; and U.S. application Ser. No. 16/258,519, titled "Manually Adjustable Device", filed concurrently herewith.

FIELD OF THE INVENTION

This invention applies to the field of cardiac surgery and more specifically, to treatment of a heart valve.

BACKGROUND OF THE INVENTION

There is broad prevalence of various organ diseases directly related to mechanical compromise of the organ tissues and/or functions. Various ones of these conditions are degenerative and progressive, for example degenerative mitral valve regurgitation. Mitral Valve Regurgitation (MR) affects 2% of the population worldwide, but less than 20% of people in developed countries who are diagnosed each year with MR undergo a cardiac surgery procedure. Left untreated, MR is a risk factor and can lead to heart failure. In addition, it is estimated that 20% of patients with heart failure and 15% of post-myocardial infarction patients have at least moderate MR.

The mitral valve is located between the left atrium and the left ventricle of the heart. During normal operation, the mitral valve opens during diastole, allowing blood to flow from the left atrium into the left ventricle. During systole, the mitral valve closes, causing high pressure blood to exit the left ventricle through the aorta. Mitral valve regurgitation is a cardiac condition in which the posterior leaflet of the mitral valve does not fully contact the anterior leaflet of the valve during systole, thus a gap remains between the leaflets of the mitral valve during systole. The gap remaining between the leaflets allows retrograde blood flow to pass from the left ventricle into the left atrium through the mitral valve. This is referred to as mitral regurgitation, or mitral valve regurgitation. Mitral regurgitation reduces the volume of blood pumped out of the heart to the aorta during each cardiac cycle, thus reducing the efficiency of the heart. Mitral regurgitation may exist for any of several reasons, including congenital malformations of the valve, ischemic disease, or effects of cardiomyopathy, such as dilated (congestive) cardiomyopathy (i.e., enlarging of the heart). Enlargement of the left ventricle of the heart with a corresponding increase in the diameter of the mitral valve annulus prevents the two leaflets of the mitral valve from co-apting and prevents them from properly preventing blood flow from the left ventricle to the left atrium during contraction of the heart.

Conventional techniques for treating dysfunctions of the mitral valve typically include highly invasive, open heart surgical procedures in order to replace or repair the dysfunctioning mitral valve. Some surgical procedures include the implantation of a replacement valve (e.g., animal valve or artificial mechanical valve). Other techniques include the use of annuloplasty rings which are surgically placed around the annulus of the mitral valve within the chamber of the heart and sutured into place. The presence of the annuloplasty ring alters the geometry of the annulus of the mitral valve in order to improve coaptation of the leaflets of the valve. Epicardial clips have also been proposed and used to alter the geometry of the annulus of the mitral valve. Another surgical technique which requires accessing one or more chambers of the heart is leaflet coaptation. Leaflet coaptation (e.g., Alfieri edge-to-edge repair) is a surgical procedure in which the valve leaflets are sutured together (e.g., bow-tie suture) to improve coaptation of the leaflets. A further surgical technique includes extending a tensioning cord across a chamber of the heart to alter the geometry of the heart chamber. The tensioning cord, which extends through a chamber of the heart, and thus is in contact with blood in the heart chamber, pulls opposing walls of the heart toward one another to reduce heart wall tension and/or reposition the papillary muscles within the chamber. These techniques typically require opening the heart and/or entering one or more of the chambers of the heart to gain direct access to the mitral valve. Recent randomized trials in heart failure and the MitraClip device found that reducing mitral regurgitation arrested the dilation of the left ventricle, common in the heart failure cycle. Grayburn et al, "Proportionate and Disproportionate Functional Mitral Regurgitation" JACC: Cardiovascular Imaging, 2018 cited that longevity and improved quality of life paralleled left ventricular volume reductions. It is reasonable that designs that reduce both mitral regurgitation and cardiac volume may have profound clinical benefits.

All of the aforementioned treatments are static approaches to treatment of the disease. That is, the configurations of the devices used to treat the disease remain fixed at the time of performing the procedure. For example, implantation of a device to treat mitral valve regurgitation results in a fixed application of force and/or configuration of the device at the time that the device is implanted. If, after implanting such a device a configuration needs to be altered or force application needs to be altered, this requires a removal of the device and re-implantation of the same device in an altered location or implantation of another, differently sized device or reconfigured device. To avoid such occurrences requires a great deal of precision with regard to the configuration/force applied by an implant device at the time of implantation. These requirements are exacerbated by procedures performed while the heart is beating.

Therefore, it may be desirable to devise a less invasive technique for treatment of diseases such as mitral valve regurgitation, wherein the treatment applied may be adjusted after fixation of an implant, but before closing the patient to complete the implantation procedure.

It may be further desirable to provide devices that include components that can be implanted under direct visualization by a surgeon, with completion of the implantation being performed when the surgeon can no longer directly visualize the location where implantation is being completed.

It may further be desirable to provide adjustable devices which maintain a desired configuration after adjustment, without concern for changing configuration after completion of the adjustment.

It may be desirable to devise a device, assembly and/or method useful in altering and/or reshaping the annulus of the mitral valve and/or the ventricle of a heart without the need to gain access to the interior of the heart, and which can be adjusted after fixation to the heart to alter and/or reshape the annulus and/or ventricular geometry so as to maintain satisfactory abatement or reduction of mitral regurgitation.

It may further be desirable to provide devices that can be minimally invasively implanted and/or which allow procedural reversibility and/or adjustment.

SUMMARY OF THE INVENTION

The present invention relates to a system for valve repair that decreases the diameter of the heart in the septal lateral direction and/or anterior posterior direction and brings the leaflets of a valve back to a normal anatomical position. The system does this by gently squeezing from the surface of the heart using a multi-step delivery method which may optionally use a multi-step delivery system to implant an epicardial device.

In one aspect of the present invention, an epicardial device for reducing or preventing regurgitation of blood through a valve of a heart is provided that includes: a main body having a segment adapted to apply force to an epicardial surface of the heart; a member that applies counterforce to said force applied by the segment; a foundation configured to be anchored to the epicardial surface of the heart, the foundation comprising a surface configured with attachment features; and the device further including a surface configured with mating attachment features configured to attach to the attachment features of the foundation; wherein the mating attachment features and attachment features are separable and reattachable to allow repositioning of at least a portion of the device relative to the foundation.

In at least one embodiment, the epicardial device includes a flap extending from the segment, the flap including a mating surface configured with the mating attachment features.

In at least one embodiment, the segment comprises a rigid structural rib contained within a pad; wherein the pad comprises a contact surface configured to apply the force to the epicardial surface.

In at least one embodiment, the segment comprises a pad; wherein the pad comprises a contact surface configured to apply the force to the epicardial surface; and wherein the flap extends inferiorly from the pad.

In at least one embodiment, the pad is configured to apply force to a posterior surface of the heart at a location superior to a location where the foundation is configured to be anchored.

In at least one embodiment, a rigid structural rib is contained within the pad.

In at least one embodiment, the flap is reattachable to the foundation to change a distance between the foundation and the segment.

In at least one embodiment, the epicardial device is configured for reshaping an annulus of a mitral valve of the heart.

In at least one embodiment, the epicardial device is configured for reshaping one or more dimensions of a left ventricle of the heart.

In at least one embodiment, the epicardial device is configured for reshaping an annulus of a tricuspid valve of the heart.

In at least one embodiment, the epicardial device is configured for reshaping one or more dimensions of a right ventricle of the heart.

In at least one embodiment, the segment comprises a posterior segment adapted to be contacted to a posterior surface of the heart, the member comprises an anterior segment configured to be contacted to an anterior surface of the heart, and the main body further comprises a lateral segment joining the anterior segment and the posterior segment.

In at least one embodiment, an annulus of a mitral valve lies in a plane between a left atrium and a left ventricle of the heart, the anatomy of the heart includes an aorta, a pulmonary trunk, a superior vena cava, a transverse sinus, an oblique sinus, and an atrioventricular groove; the anterior segment is configured to be positioned in the transverse sinus of the heart; the posterior segment is configured to be positioned on or inferior to the atrioventricular groove of the heart; and the lateral segment extends between the anterior segment and the posterior segment.

In at least one embodiment, the foundation comprises a first foundation, the epicardial device further comprising a second foundation, wherein the second foundation is configured to be anchored to the epicardial surface of the heart at a location inferior to a location where the first foundation is configured to be anchored; the second foundation comprising a second surface configured with second attachment features; and the device further comprising a surface configured with second mating attachment features configured to attach to the second attachment features of the second foundation; wherein the second mating attachment features and second attachment features are separable and reattachable to allow repositioning of at least a second portion of the device relative to the second foundation.

In at least one embodiment, the epicardial device includes a flap extending from the segment and an extension extending from one of the segment or the flap; wherein the extension is reattachable to the second foundation to change a distance between the second foundation and the first foundation.

In at least one embodiment, the epicardial device further includes a third foundation, wherein the third foundation is configured to be anchored to the epicardial surface of the heart at a location inferior to a location where the first foundation is configured to be anchored and separate from a location where the second foundation is configured to be anchored; the third foundation comprising a third surface configured with third attachment features; and the device further comprising a surface configured with third mating attachment features configured to attach to the third attachment features of the third foundation; wherein the third mating attachment features and third attachment features are separable and reattachable to allow repositioning of at least a third portion of the device relative to the third foundation.

In at least one embodiment, the epicardial device includes a flap extending from the segment and a first extension extending from one of the segment or the flap; and a second extension extending from one of the segment or the flap;

wherein the first extension is reattachable to the second foundation to change a distance between the second foundation and the first foundation; and wherein the second extension is reattachable to the third foundation to change a distance between the third foundation and the first foundation.

In another aspect of the present invention, an epicardial device for placement on the epicardial surface of a heart in order to reshape the annulus of the mitral valve of the heart is provided, the mitral valve lying in a plane between the left atrium and the left ventricle of the heart, the anatomy of the heart includes an aorta, a pulmonary trunk, a superior vena cava, a transverse sinus, and an atrioventricular groove. The epicardial device includes: an anterior segment, a posterior segment and a lateral segment extending between the anterior segment and the posterior segment; wherein the anterior segment is configured and dimensioned to at least partially occupy the transverse sinus epicardially; wherein the lateral segment is configured for positioning the anterior segment on or above a plane in which the mitral valve is located, and the posterior segment on or below the plane in which the mitral valve is located, and below a position of the anterior segment; wherein the posterior segment is configured to apply a force to a posterior epicardial surface of the heart; a foundation configured to be anchored to the posterior epicardial surface of the heart, the foundation comprising a surface configured with attachment features; and the device further comprising a surface configured with mating attachment features configured to attach to the attachment features of the foundation; wherein the mating attachment features and attachment features are separable and reattachable to allow repositioning of at least the posterior segment relative to the foundation.

In at least one embodiment, the epicardial device includes a flap extending from the posterior segment, the flap comprising a mating surface configured with the mating attachment features, wherein the flap is attachable, detachable and reattachable to and from the foundation to affect a change in position of at least the posterior segment relative to the foundation when the foundation is anchored.

In at least one embodiment, the foundation comprises a first foundation, the epicardial device further comprising a second foundation, wherein the second foundation is configured to be anchored to the epicardial surface of the heart at a location inferior to a location where the first foundation is configured to be anchored; the second foundation comprising a second surface configured with second attachment features; and the device further comprising a surface configured with second mating attachment features configured to attach to the second attachment features of the second foundation; wherein the second mating attachment features and second attachment features are separable and reattachable to allow repositioning of at least a second portion of the device relative to the second foundation.

In at least one embodiment, the epicardial device includes a flap extending from the segment and an extension extending from one of the posterior segment or the flap; wherein the second foundation is configured to be attached to the epicardial surface of the heart; wherein the extension is reattachable to the second foundation to apply forces to the epicardial surface to reduce tension on chordae tendineae of the heart.

In at least one embodiment, the epicardial device further includes a third foundation, wherein the third foundation is configured to be anchored to the epicardial surface of the heart at a location inferior to a location where the first foundation is configured to be anchored and separate from a location where the second foundation is configured to be anchored; the third foundation comprising a third surface configured with third attachment features; and the device further comprising a surface configured with third mating attachment features configured to attach to the third attachment features of the third foundation; wherein the third mating attachment features and third attachment features are separable and reattachable to change force applied between the third foundation and the posterior segment.

In another aspect of the present invention, a method of epicardial treatment of valve regurgitation associated with a valve of a heart of a patient includes: establishing at least one opening in the patient to provide access to the heart; applying an epicardial force on a location of the heart, while visualizing regurgitation through the valve via visualization apparatus; varying at least one of the location or the amount of epicardial force applied to identify a target position where valve regurgitation is reduced or eliminated; marking the target position; anchoring a foundation to the epicardial surface of the heart to provide a base for fixing an epicardial device thereto; and fixing the epicardial device to the foundation, wherein the fixing establishes a segment of the device in the target position and wherein the fixing indirectly fixes the epicardial device to the heart.

In at least one embodiment, the method includes visualizing functioning of the valve after the fixing the epicardial device; detaching the epicardial device from the foundation when the further visualizing shows an unacceptable amount of regurgitation; repositioning the epicardial device to reduce the amount of regurgitation and verifying reduction in regurgitation by the further visualizing; and re-attaching the epicardial device to the foundation.

In at least one embodiment, the foundation comprises a first foundation, and the method further includes: anchoring a second foundation to the epicardial surface of the heart; and attaching an extension between the second foundation and one of the first foundation or the segment to apply compression forces between the second foundation and the one of the first foundation or the segment to reduce tension on chordae tendineae of the heart.

In at least one embodiment, the valve is the mitral valve, the segment comprises a posterior segment, the epicardial device further comprises an anterior segment, an anterior end, a posterior end and a lateral segment extending between the anterior segment and the posterior segment; wherein the anterior and posterior segments are positioned epicardially on the heart at locations apposite to an annulus of the mitral valve, such that the anterior and posterior segments apply force sufficient to reshape the annulus.

In at least one embodiment, the method further includes: measuring a distance between opposing epicardial surfaces of the heart where one of the opposing epicardial surfaces is measured at the target position; and selecting the epicardial device so that the epicardial device is configured with opposed force applying segments separated by a distance that approximates the measured distance between the opposing epicardial surfaces, when the epicardial device is installed on the heart and fixed to the foundation.

In at least one embodiment, the method further includes: measuring an unobstructed length of a transverse sinus of the heart; and providing the epicardial device to have an anterior segment length less than or equal to the unobstructed length, wherein the anterior segment is positioned in the transverse sinus prior to the fixing.

In another aspect of the present invention, a method of epicardial treatment of mitral valve regurgitation associated with a mitral valve of a heart of a patient is provided, the anatomy of the heart including an aorta, a pulmonary trunk, a superior vena cava, a transverse sinus, a left atrial appendage, and an oblique sinus. The method includes: applying an epicardial force on a posterior location of the heart, while visualizing regurgitation through the valve via visualization apparatus; varying at least one of the location or the amount of epicardial force applied to identify a target position where mitral valve regurgitation is reduced or eliminated;

marking the target position; lifting the heart at least partially out of a chest cavity of the patient to allow direct visualization of the marking; anchoring a foundation to the epicardial surface of the heart at a location having a predefined relationship to the marking; providing a clip having an anterior segment, an anterior end, a posterior segment, a posterior end and a lateral segment extending between the anterior segment and the posterior segment; positioning the anterior and posterior segments epicardially on the heart at locations apposite to an annulus of the mitral valve, such that the anterior and posterior segments apply force sufficient to reshape the annulus, wherein the posterior segment is located on the target position; fixing the clip to the foundation, wherein the fixing maintains the posterior segment in the target position.

In at least one embodiment, the anterior segment is at least partially inserted into a transverse sinus of the heart and the transverse sinus maintains a position of the anterior segment.

In at least one embodiment, the method further includes: lowering the heart to return it to a position in the chest cavity; further visualizing functioning of the mitral valve; detaching the clip from the foundation to allow repositioning the clip to reduce an amount of mitral regurgitation; repositioning the clip to reduce the amount of regurgitation and verifying reduction in regurgitation by the further visualizing; and re-attaching the clip to the foundation.

In at least one embodiment, the method further includes: anchoring a second foundation to the epicardial surface of the heart at a second location; attaching an extension to the second foundation, the extension extending from one of the foundation or the clip, to establish a compression force between the second foundation and the one of the foundation or the clip, to reduce tension on chordae tendineae of the heart.

In at least one embodiment, the method further includes: lowering the heart to return it to a position in the chest cavity; detaching the extension from the second foundation; and re-attaching the extension to the second foundation in a relative position to vary the amount of reduction in tension on the chordae tendineae.

In another aspect of the present invention, a minimally invasive method for epicardial implantation of a device for treatment of valve regurgitation, is provided, the method including: installing a device port, a camera port and at least one instrument port in the chest of a patient to permit access to a chest cavity of the patient by the device, a camera and instruments; insufflating the chest cavity; positioning the camera though the camera port and into the chest cavity; introducing a foundation through one of the ports; anchoring the foundation to an epicardial surface of the heart; introducing the device through the device port and into the chest cavity using an instrument controlled from outside the chest cavity and device port; manipulating the device to partially surround an annulus of a valve by placement of the device on epicardial walls of the heart at locations that partially surround the annulus; and anchoring the device to the epicardial walls of the heart at least in part by attaching a portion of the device to the anchored foundation.

In at least one embodiment, the method further includes: prior to introducing the foundation, assessing a width measurement for selecting a device having opposing contact surfaces defining a width that most closely matches the width measurement wherein the assessing comprises: passing a width measuring instrument through the device port; positioning and manipulating the width measuring instrument to apply forces to an epicardial surface of the heart in a plane of the valve to be treated, while visualizing functioning of the valve to assess any regurgitation that may be occurring; repositioning the width measurement instrument and/or varying an amount of force applied by the width measurement instrument while continuing said visualizing; identifying a location where the width measurement instrument is applied to the epicardial surface where regurgitation is minimized or eliminated. measuring the width between the location, as presently deformed by the width measurement instrument in the identified location, with a force used at the identified location to establish the minimization or elimination of regurgitation and a location opposite the identified location, on an opposite epicardial surface; removing the width measuring instrument from the chest cavity, out of the device port; and selecting the device having opposing contact surfaces defining a width that most closely matches the width measurement.

In at least one embodiment, the foundation is attached at a location having a predefined relationship relative to the identified location.

In at least one embodiment, the valve being treated is a mitral valve, and the method includes: prior to introducing the device, assessing an anterior-posterior dimension of a transverse sinus of the heart, wherein the assessing includes: inserting a length sizing instrument through one of the ports with a manipulating instrument operated from outside of the port; manipulating the length sizing instrument with the manipulating instrument to insert the length sizing instrument into the transverse sinus; inserting the length sizing instrument to extend over a usable length of the transverse sinus that does not include an obstruction; reading a length measured by the length sizing instrument when fully inserted in the usable length; removing the length sizing instrument from the chest cavity; and selecting the device that has an anterior arm having a best match to the length measured.

In at least one embodiment, the reading comprises grasping the length sizing instrument with an instrument and reading a measurement along a gradient scale on the length sizing instrument, using the camera, wherein the reading is taken at a location where the length sizing instrument is at an open end of the transverse sinus.

In at least one embodiment, the valve being treated is a tricuspid valve.

These and other advantages and features of the invention will become apparent to those persons skilled in the art upon reading the details of the devices and methods as more fully described below.

BRIEF DESCRIPTION OF THE DRAWINGS

In the course of the detailed description to follow, reference will be made to the attached drawings. These drawings show different aspects of the present invention and, where appropriate, reference numerals illustrating like structures, components, materials and/or elements in different figures are labeled similarly. It is understood that various combinations of the structures, components, materials and/or elements, other than those specifically shown, are contemplated and are within the scope of the present invention.

DETAILED DESCRIPTION OF THE INVENTION

Figure 1A:
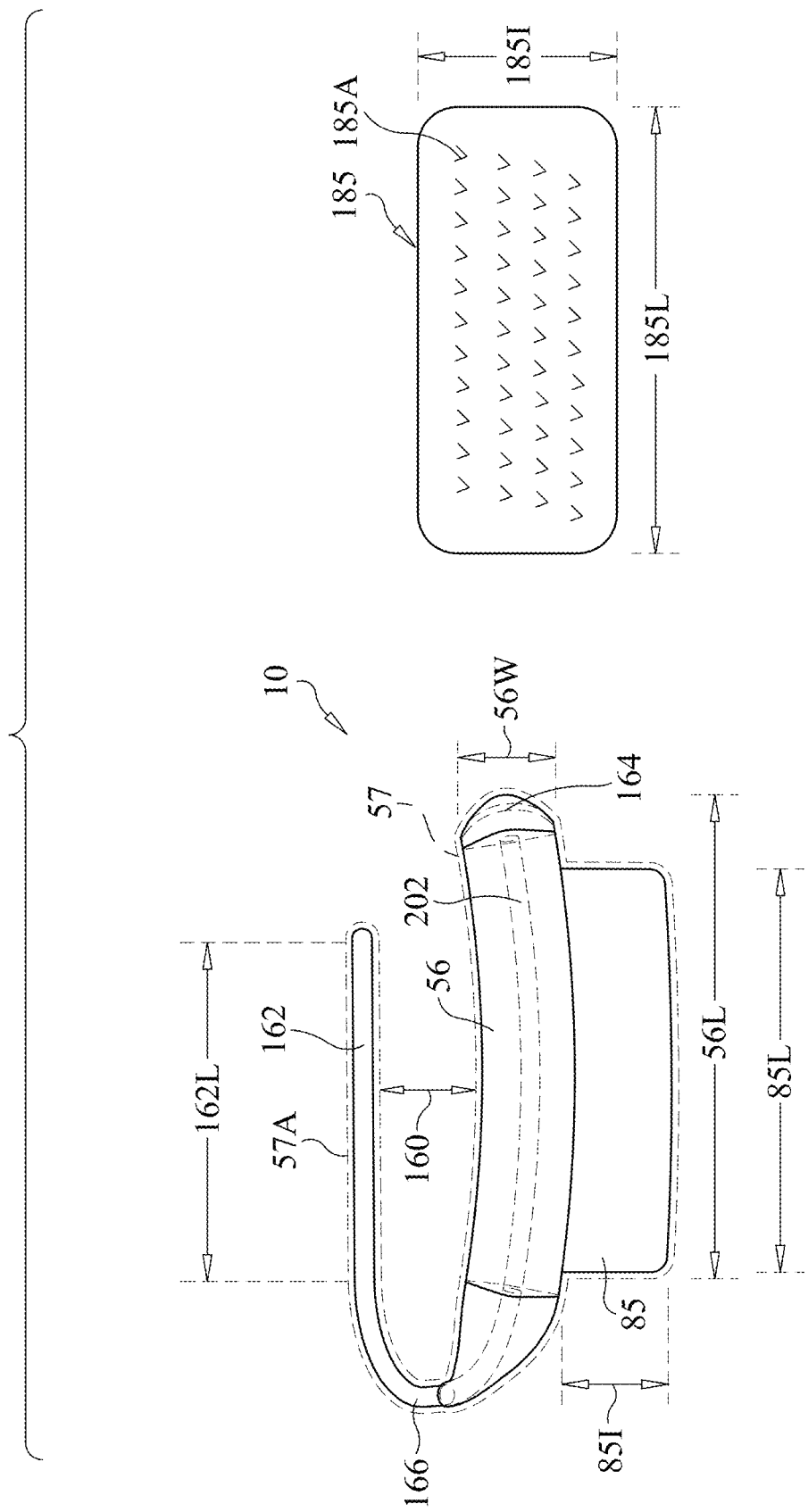
FIG. 1A is a posterior, perspective view of an epicardially implantable device, according to an embodiment of the present invention.

Before the present devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a tack" includes a plurality of such tacks and reference to "the foundation" includes reference to one or more foundations and equivalents thereof known to those skilled in the art, and so forth.

The publications discussed herein are provided solely for their disclosure prior to the filing date of the present application. The dates of publication provided may be different from the actual publication dates which may need to be independently confirmed.

Definitions

As used in the specification and the appended claims, the term "anterior" is used in its anatomical sense to mean "toward the front, in front of, or the front surface of."

As used in the specification and the appended claims, the term "posterior" is used in its anatomical sense to mean "toward the back, in back of, or the back surface of."

As used in the specification and the appended claims, the term "superior" is used in its anatomical sense to mean "above, over top of, directed upward or toward the head."

As used in the specification and the appended claims, the term "inferior" is used in its anatomical sense to mean "below, underneath, directed downward or toward the feet."

As used in the specification and the appended claims, the term "lateral" is used in its anatomical sense to mean "a position or direction farther from the sagittal or median plane or midline of the body, to the side of, or the side surface of."

DETAILED DESCRIPTION

Devices, apparatus and methods are provided for implantation to reduce the size of an annulus to correct coaptation of valve leaflets within the annulus that have been rendered dysfunctional by an enlargement of the annulus. In at least one embodiment, an epicardial clip for placement on the epicardial surface of a heart in order to reshape the annulus of the mitral valve of the heart is provided, the mitral valve lying in a plane between the left atrium and the left ventricle of the heart, the anatomy of the heart includes an aorta, a pulmonary trunk, a superior vena cava, a transverse sinus, and an atrioventricular groove.

Epicardial devices, when implanted may apply force to both anterior and posterior (and potentially, lateral) surfaces of the heart to translate these forces for the desired reshaping of the annulus and/or ventricle. Methods described herein may include an observation stage during which manual force is applied to a posterior surface of the heart, while using visualization techniques to determine a target location and amount of force (resulting in an amount of deformation of the heart wall) that is sufficient to eliminate or satisfactorily reduce an amount of regurgitation through the valve leaflets that an annulus affected by the deformation surrounds. This observation stage may be used to determine a size of an implant to be implanted, as well as the position (target location) on the posterior surface of the heart that the posterior segment of the device is to be implanted. The heart can then be lifted up and partially out of the chest cavity, so that the posterior segment can be implanted in the target location that has been identified. This poses potential problems, as it is often difficult to observe the exact location or footprint of the application of force to the posterior surface. Even when an accurate observation of the footprint can be made, it still may be difficult to accurately locate the posterior portion of the device on the footprint, as it is difficult, if not impossible to directly visualize the placement of the device relative to the posterior surface. Once the posterior portion/segment is attached and the heart is repositioned to its original location, there may therefore be a greater amount of regurgitation occurring than what was observed during the observation stage. In such instances, this may require a repositioning of the posterior segment to a more optimal location that further reduces regurgitation, or in worse cases, complete replacement of the implant by an implant having a different width dimension between the anterior and posterior segments than that which was originally used. In either case, the repositioning or replacement of the posterior segment/implant involves removing screws, tacks or other fixation means that were used to fix the original posterior segment, and then reattachment of the posterior segment or replacement posterior segment, again with screws, tacks or other fixation means. The removal of the fixation means results in bleeding from the heart wall, which can cause further complications to the procedure, not limited to decreased visibility for continuing steps in the procedure, increased risk of infection, and/or longer healing times. The present invention eliminates these risks and provides the surgeon with the ability to anchor and adjust the posterior portion of the implant with much greater ease, safety and with a significant reduction in the time than would be otherwise required for re-implantation/repositioning as described. Such adjustment can be performed even after anchoring the device epicardially to the heart, thereby eliminating the need to remove and implant and reinstall it with a different or reconfigured implant. This also eliminates the need to remove tissue anchors. Still further, the present invention allows procedures, after completion of implantation, to reenter the target site to manually adjust the device to change the location of the posterior segment and thereby alter the direction of the force and possibly the amount of force as applied thereby, to restore the successful reduction or elimination of valve regurgitation. With these procedures, it is not necessary to remove the device or even to remove the tissue anchors.

FIG. 1A is a posterior, perspective view of an epicardially implantable device 10 according to an embodiment of the present invention. In this embodiment, device 10 may have a generally U-shape or C-shape when viewed from a top or bottom view, and which can also be seen in this perspective orientation. The device 10 may be shaped such that the distance 160 across the device 10A between the contact surface of the anterior segment 162 and the contact surface of the posterior segment 164 defines the space between which the mitral valve and mitral valve annulus (as well as the heart walls apposite these features) will be located after implantation of the device 10 and may determine the final anterior-posterior diameter of the mitral valve annulus. The anterior segment 162 may be substantially straight, and thus capable of residing in the transverse sinus of the heart. The posterior segment 164 may be arcuate, corresponding to the convex curvature of the posterior ventricular wall of the heart in a location where it is designed to be positioned for implantation. The lateral segment 166 interconnects the anterior 162 and posterior 164 segments with a sufficient length to establish the appropriate distance 160 between the segments 162 and 164 for effectively applying force to the mitral valve annulus 22A to cause a reduction or elimination of mitral valve regurgitation. The main body or frame 202 of device 10 extends through all segments 162, 164 and 166 and is non-flexible and rigid to an extent wherein the conformation shown is not readily deformed and is not deformed by the forces applied to it by the beating heart when it is implanted. In this embodiment, frame 202 is formed by a metal wire, preferably out of titanium or titanium alloy, but could alternatively be formed from other biocompatible metals such as stainless steel, such as 304V, 304L, and 316LV stainless steel; mild steel; nickel-titanium alloy such as linear-elastic and/or super-elastic nitinol; other nickel alloys such as nickel-chromium-molybdenum alloys, and the like.

The posterior segment 164 in this embodiment includes a pad 56 which is preferably compliant and is atraumatic when contacted to target tissue such as the heart. Pad 56 may be formed as an over-mold of silicone or other compliant, biocompatible material. Pad 56 encases at least a portion of, preferably substantially the entire posterior segment portion of the frame (rod) 220. Pad 56 is preferably made from silicone, but could alternatively be made from other moldable, biocompatible polymers. Alternatively, device 10 may be provided with the posterior segment 164 having no pad, so that the main frame 202 forms the posterior segment 164. Further alternatively, the pad 56 may be encapsulated by a sheath 57, or, if the pad 56 is not included, the main frame 202 of the posterior segment may be encapsulated by a sheath 57. Still further alternatively, all segments 162, 164 and 166 may be encapsulated by a sheath 57A with or without presence of the pad 56. In some embodiments, for example, sheath 57 may be an ePTFE material, non-molded fluorinated ethylene propylene (FEP), a polyester knitted fabric, a polyester velour, a polypropylene felt, a woven or braided fabric, a non-woven fabric, porous material, or other textile material, as desired. Sheath 57 may promote tissue in-growth on the epicardial surface of the heart, may provide tissue in-growth into interstices of the fabric sheath 133, and/or provide adequate frictional forces (traction) to hold the clip 110 in contact with the heart and prevent migration of the device once positioned on the heart. Tissue in-growth therein and/or thereon may provide long-term retention of the clip 110 in a desired position on the heart and prevent erosion.

In some embodiments, device 10 may include a drug eluting coating in addition to or as an alternative to sheath 57. The drug eluting coating may a controlled release of a therapeutic agent over a specified period of time. The therapeutic agent may be any medicinal agent which may provide a desired effect. Suitable therapeutic agents include drugs, genetic materials, and biological materials. Some suitable therapeutic agents which may be loaded in the drug eluting coating include, but are not necessarily limited to, antibiotics, antimicrobials, antioxidants, anti-arrhythmics, cell growth factors, immunosuppressants such as tacrolimus, everolimus, and rapamycin (sirolimus), therapeutic antibodies, wound healing agents, therapeutic gene transfer constructs, peptides, proteins, extracellular matrix components, steroidal and non-steroidal anti-inflammatory agents, antiproliferative agents such as steroids, vitamins and restenosis inhibiting drugs, such as Taxol®, paclitaxel (i.e., paclitaxel, paclitaxel analogues, or paclitaxel derivatives, and mixtures thereof).

A flap 85 extends inferiorly from the pad 56 of posterior portion 164 in the embodiment of FIG. 1A. Flap 85 functions to anchor the posterior portion 164 to the posterior wall of the heart by attachment to foundation 185 as described in more detail below. Flap 85 may be formed integrally with pad 56 and may be of the same or different material. Typically the flap is made of a material described above for use in making sheath 57. Flap 85 may be attached directly to the main frame 202 in embodiments where a pad 56 is not employed. Flap 85 may be manufactured separately and then mechanically and/or chemically fixed to pad 56 or main frame 202.

A foundation 185 is separately provided and is configured to be implanted to the surface of the heart, such as by anchoring using tacks, screws or other equivalent fixation means. Foundation 185 is a thin structure that can be fixed to the heart wall prior to anchoring the posterior segment 164. For example, foundation 185 may be made from a thin layer of silicone or other structural core layer to provide structure thereto, which may then be covered with any of the same materials described above for use in making sheath 57. Alternative materials could be used that are biocompatible and flexible, but which have sufficient rigidity to provide structural support to the foundation, such that it can be deformed to conform to the curvature of the surface of the heart that it is being anchored to, but retains sufficient rigidity so that it does not buckle, wrinkle, or otherwise deform from its conforming shape. Optionally that core of the foundation may not be covered. For example, when the desired target location for fixation of the posterior segment is identified (described in more detail below), the foundation can then be implanted on the heart wall in a location that will fix the posterior segment in the target location when flap 85 is attached to foundation 185. To establish the attachment of flap 85 to foundation 185, the surfaces of the flap 85 and foundation 185 that come into contact with one another to accomplish the attachment are provided with mating attachment features 85A, 185A.

Figure 1B:
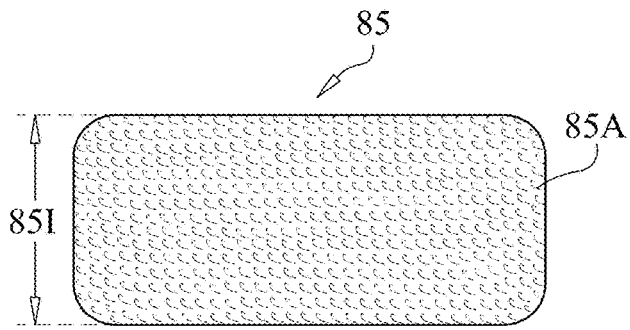
FIG. 1B shows the opposite surface of the flap shown in FIG. 1A.
Figure 1C:
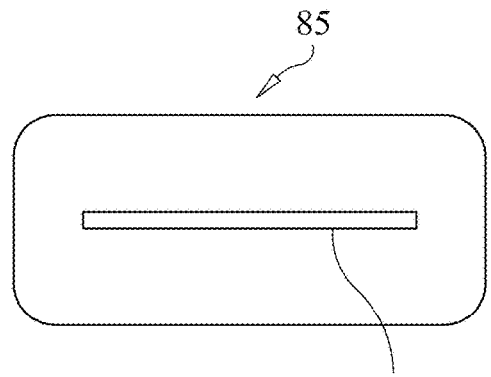
FIGS. 1C and 1D illustrate the flap and foundation of FIG. 1A provided with alternative attachment features, according to an embodiment of the present invention.
Figure 1D:
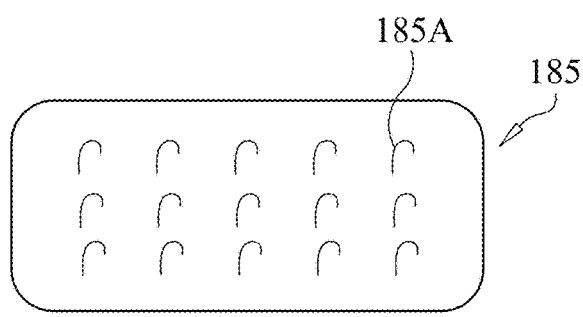

In the embodiment of FIGS. 1A-1B the attachment features are hook-and-loop type fasteners, such as VELCRO®, with the hook type features provided as 185A and the loop type features provided as 85A. Alternatively, 85A could be hook type features and 185A could be loop type features. FIG. 1B shows the reverse surface of the flap 85 shown in FIG. 1A, which is the surface that interfaces with the outer surface of the foundation (faces outwardly from the heart surface when foundation 185 is implanted on the heart surface), shown in FIG. 1A. The surface area of the outer surface of foundation 185 may be equal to, less than or greater than the surface area of the surface of flap 85 that it interfaces with. Preferably, the superior-inferior dimension 185I of foundation 185 is greater than the superior-inferior dimension 85I to better support adjustment of the flap 85 in the inferior-superior direction relative to the foundation 185, although this is not necessary. In FIG. 1A the hooks of the hook type fasteners face in the inferior direction to facilitate movement of the flap 85 inferiorly relative to the foundation 185 so that less force is required for adjustment movement in that direction. However, the hook orientations could alternatively face superiorly, laterally, in any directions, in multiple directions, or randomly. Further alternatively, other types of attachment features may be substituted that still attach the flap 85 and foundation 185 with sufficient holding force to maintain the flap 85 and foundation 185 fixed with respect to one another over the lifetime of the implantation, as do the hook and loop type fasteners, but also allow the surgeon (or other operator) to manually detach the flap from the foundation and reattach the flap 85 to the foundation 185, if needed, without the requirement of removing any attachment features from the tissue of the heart. Examples of such alternatives include, but are not limited to: magnets, restickable glue, multiple rows of snaps, or the like. FIGS. 1C and 1D show another alternative arrangement in which the flap 85 is provided with a bar or rod 85A spaced from the surface of the flap 85 to allow it to be captured by hooks 185A mounted on foundation 185 as illustrated in FIG. 1D. In this embodiment, the flap 85 can be positioned in one of three different rows of hooks 185A to vary the inferior/superior position of the flap 85 relative to the foundation 185. Of course, this embodiment is not limited to three rows of hooks, as two rows or more than three rows could be incorporated.

The lengths and orientations of the anterior 162, posterior 164 and lateral 166 segments may include any of those described in US Patent Application Publication No. 2012/0323314 which is hereby incorporated herein, in its entirety, by reference thereto. For example, the length 56L of the posterior segment 164 may be in the range of 25 mm to 80 mm, in the range of 31 to 70 mm, in the range of 38 mm to 64 mm, or in the range of about 39 mm to about 64 mm, in some instances in the range from 30 mm to 40 mm, from 40 mm to 50 mm, from 45 mm to 55 mm, from 33 mm to 37 mm, from 43 mm to 47 mm, from 48 mm to 53 mm, in some instances 30 mm, 35 mm, 40 mm, 45 mm or 50 mm. The width of the posterior segment/pad 56W may be in the range of 5 mm to 30 mm, in the range of 8 mm to 25 mm, in the range of 10 mm to 20 mm, or 12 mm to 18 mm or 13 mm to 17 mm or 14.5 to 15.5 mm in some instances. The posterior segment 164 may have a radius of curvature extending along the length thereof that is variable and designed to conform to the contour of the heart wall against which it is intended to apply force. The largest radius of curvature along the length direction of the contact surface (surface of 164 facing into page in FIG. 1A) may be in the range of 50 mm to 130 mm, 40 mm to 115 mm, 75 mm to 105 mm, or about 73 mm to 104 mm in some instances.

The anterior segment 162 has a length 162L designed so that the anterior segment 162 can be received in the transverse sinus, and so that with the lateral segment 166 contacting the surface of the heart, the free end of anterior segment 162 extends as far into the transverse sinus as possible without obstructing a pulmonary vein or other structure that could be extending into the transverse sinus. Anterior segment 162, may be a straight segment, such as illustrated in FIG. 1A and length 162L may be in the range from 40 mm to 80 mm, in the range from 45 mm to 50 mm, in the range from 50 mm to 55 mm, 55 mm to 60 mm, 60 mm to 65 mm, 65 mm to 72 mm, 72 mm to 80 mm or in the range from 40 mm to 85 mm in some instances. In one specific, non-limiting embodiment, at least two devices 10 are provided in a kit, the first device having a length 162L different from a length 162L of a second device 10 and the first and second devices have equal width measurements 160. In another non-limiting embodiment, at least two devices 10 are provided in a kit, the first device having a length 162L equal to a length 162L of a second device 10 and the first and second devices have unequal width measurements 160. In another non-limiting embodiment, at least two devices 10 are provided in a kit, the first device having a length 162L different from a length 162L of a second device 10 and the first and second devices have unequal width measurements 160. In one specific, non-limiting embodiment, at least two pairs of devices 10 are provided wherein a first pair has equal width measurements 160 and unequal length measurements, and the second pair has equal width measurements 160 to each other (but unequal to the width measurement 160 of the first pair) and unequal length measurements. 162L. In at least one embodiment, the unequal length measurements 162L are also unequal to each of the length measurements 162L of the second pair. In at least one embodiment, at least one of the unequal measurements 162L is equal to one of the unequal measurements 162L of the second pair. More than a pair of devices 10 having the same width measurement 160 may be provided, with each having a length measurement 162L different from the others. More than two different width 160 sizes of devices may also be provided, wherein multiple ones of each particular width size 160 each have a different length 162L: In one specific example, two devices 10 having a width of 35 mm were provided with a first of these devices 10 having a length 162L of 55 mm and the second having a length of 48 mm; two devices 10 having a width of 40 mm were provided with a first of these devices 10 having a length 162L of 63 mm and the second having a length of 56 mm; two devices 10 having a width of 45 mm were provided with a first of these devices 10 having a length 162L of 70 mm and the second having a length of 63 mm; and two devices 10 having a width of 50 mm were provided with a first of these devices 10 having a length 162L of 78 mm and the second having a length of 70 mm. Optionally, a third device 10 having a width of 50 mm had a length 162L of 63 mm.

Flap 85 extends inferiorly from the pad 56 or main body 202 by a distance 85I that, together with the length 85L establishes a surface area sufficient to mate with the opposing surface area 185 in an amount sufficient to fix the components together so that they remained fixed unless the surgeon/installer purposely separates them for readjustment or replacement. For example the length 85L may be about the same or slightly less than length 56L, but need not be, as it could be much less than 56L. Width 85I is typically less than length 85L, typically in a range from about 30% to 90% of length 85L, more typically from about 40% to 70% of length 85L, although width values may vary from these typical ranges. The width 185I of foundation 185 may be in a range from about 25% to 200% of width 85I, but is typically about the same as width 85I. Preferably, the superior-inferior dimension 185I of foundation 185 is greater than the superior-inferior dimension 85I to better support adjustment of the flap 85 in the inferior-superior direction relative to the foundation 185, although this is not necessary. Typically the attachment features are strong enough in shear strength so that the size of the foundation 185 does not have to be greater than the size of the flap 85. The surface area of the flap 85 where attachment features are attached to mating attachment features on the foundation 185 needs to be large enough to provide sufficient shear strength by the mating attachment features, so that forces thereagainst by the posterior arm 164 pulling upward toward the transverse sinus and away from the apex of the heart does not overcome the shear strength of the mating attachment features.

Device 10 may be configured so that the lateral segment 166 can be routed around the left lateral side of the heart, placing the anterior segment 162 in the transverse sinus and the posterior segment 164 on the posterior of the heart, such as on or inferior to the atrioventricular groove or in the oblique sinus of the heart. In some embodiments the lateral segment 166 may be routed around, over and/or under the left atrial appendage of the heart. In other embodiments, the lateral segment 166 may be routed over the left atrium of the heart.

In some variants of this and all other embodiments described herein, the device may include a drug eluting coating in addition to pad 56. The drug eluting coating may be provided in addition to a sheath or as an alternative to the sheath. The drug eluting coating may a controlled release of a therapeutic agent over a specified period of time. The therapeutic agent may be any medicinal agent which may provide a desired effect. Suitable therapeutic agents include drugs, genetic materials, and biological materials. Some suitable therapeutic agents which may be loaded in the drug eluting coating include, but are not necessarily limited to, antibiotics, antimicrobials, antioxidants, anti-arrhythmics, cell growth factors, immunosuppressants such as tacrolimus, everolimus, and rapamycin (sirolimus), therapeutic antibodies, wound healing agents, therapeutic gene transfer constructs, peptides, proteins, extracellular matrix components, steroidal and non-steroidal anti-inflammatory agents, anti-proliferative agents such as steroids, vitamins and restenosis inhibiting drugs, such as TAXOL®, paclitaxel (i.e., paclitaxel, paclitaxel analogues, or paclitaxel derivatives, and mixtures thereof).

Figure 2:
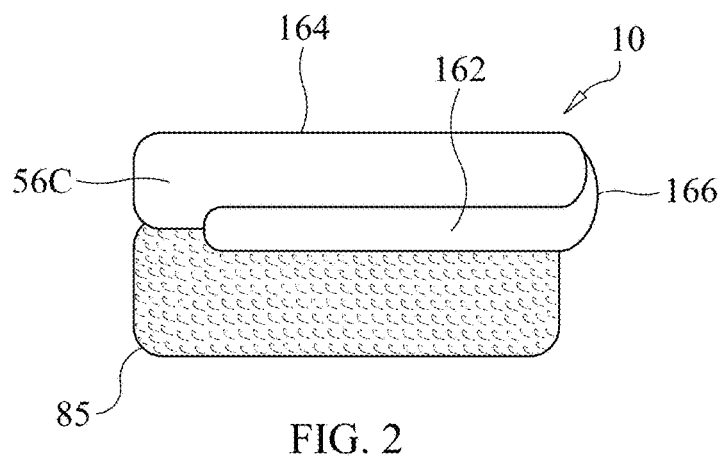
FIG. 2 is an anterior, perspective view of the device clip shown in FIG. 1A.

Pad 56 includes a contact surface 56C (see anterior, perspective view of FIG. 2) that is configured to contact a posterior surface of the heart when implanted, according to this embodiment and all other embodiments. The contact surface 56C is preferably curved (but is not necessarily curved in all embodiments) to follow a contour of a posterior surface of the heart at a location where it is designed to be implanted. All corners and ends of the pad may be rounded or otherwise structured so as to be atraumatic to surrounding tissues during and after implantation of the device 10. The anterior segment 162 is configured and dimensioned to at least partially occupy the transverse sinus epicardially and end at a location short of overlying the right atrium; the lateral segment 166 being curved so that the anterior segment 162 can be positioned on or above a plane in which the mitral valve is located, which allows a portion of the posterior segment 164 to be positioned on or below the plane in which the mitral valve is located, wherein rotation of the device 10 about a longitudinal axis of the anterior segment 162 allows the posterior segment 164 to be moved towards or away from the apex of the heart while the anterior segment 162 remains in full contact with a base of the transverse sinus, on the epicardial surface of the heart at a location superior of an anterior annulus of the mitral valve. Preferably the frame 202 is non-flexible, having a permanent configuration which may not be readily bent to an ad hoc configuration thereby maintaining segments 162, 164 and 166 is fixed orientations relative to one another.

Figure 3A:
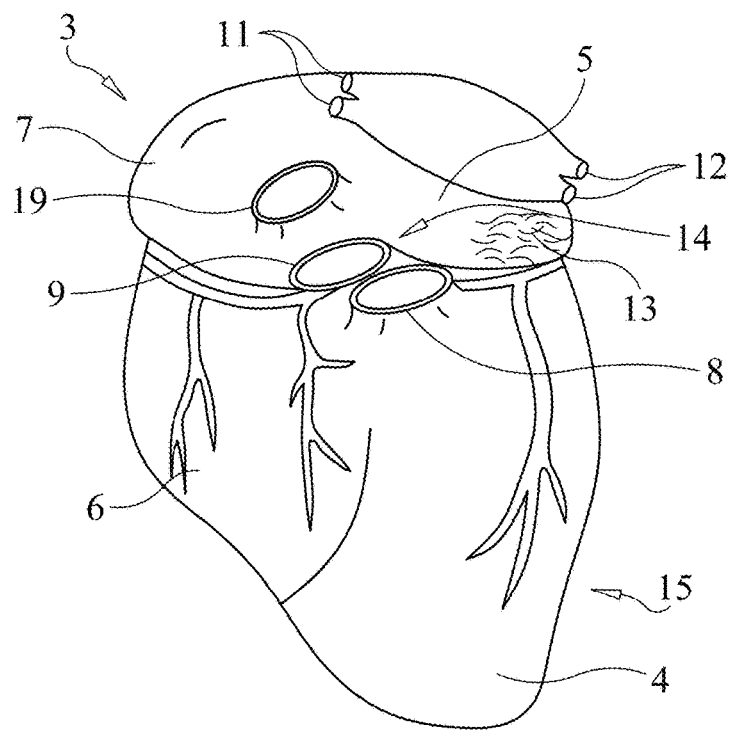
FIGS. 3A-3B are illustrations of a human heart, with the illustration in FIG. 3B viewed with the pericardium removed.
Figure 3B:
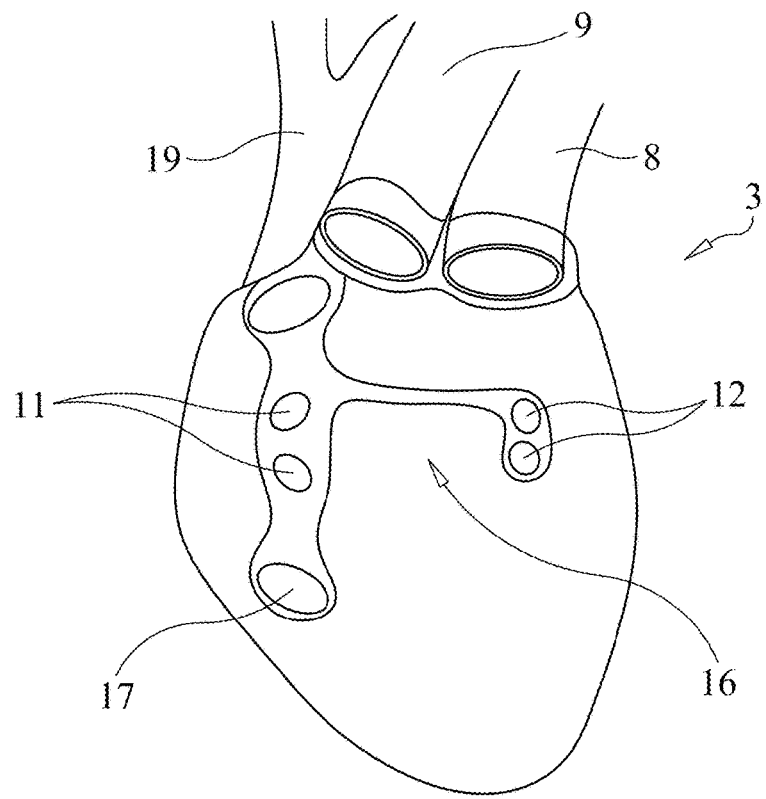

FIGS. 3A-3B are illustrations of a human heart 3, with the illustration in FIG. 3B viewed with the pericardium 15 removed. The chambers of the heart 3 include the left ventricle 4, the left atrium 5, the right ventricle 6, and the right atrium 7. Also shown are the pulmonary trunk 8, the aorta 9, the superior vena cava 19, the right pulmonary veins 11, the left pulmonary veins 12, and the left atrial appendage 13. The transverse sinus 14 is also referenced in FIG. 3A. The transverse sinus 14 is a pericardial cavity between the pericardium 15 and the epicardial surface of the heart 3 located posterior to the aorta 9 and the pulmonary trunk 8 and anterior to the left atrium 5 and the superior vena cava 19. The pericardial sac or pericardium 15, which is a tissue membrane covering the epicardial surface of the heart 3, is also shown removed from the heart 3 in FIG. 3B to further illustrate noteworthy anatomy of the heart 3. The oblique sinus 16 is a blind (e.g., cul-de-sac) recess on the posterior of the heart 3 formed between the pericardium 15 and the epicardial surface of the heart 3. The oblique sinus 16 lies generally between the right pulmonary veins 11 and the left pulmonary veins 12, with the thoracic part of the inferior vena cava 17 located on the side of the pulmonary veins 11. Only two layers of serous pericardium separate the transverse sinus 14 and the oblique sinus 16.

The devices described herein may be positioned on the epicardial surface of the heart 3 during a medical procedure. For example, in some embodiments the device 10 may be installed on the heart 3 during a beating heart surgery, without the need of a heart/lung bypass machine. For instance, the device 10 may be implanted on the heart 3 through an open chest procedure (sternotomy) or a lateral thoracotomy. In some embodiments, the device 10 may be positioned on the heart 3 through a less-invasive endoscopic approach. For example, during a sternotomy, the thoracic cavity may be accessed for direct visual placement of the device 10 on the beating heart 3. For any of these procedures, the pericardium 15 may be incised to access the pericardial cavity between the pericardium 15 and the epicardial surface of the heart 3. Upon accessing the pericardial cavity, the device 10 may be properly positioned on the epicardial surface of the heart 3.

Figure 4A:
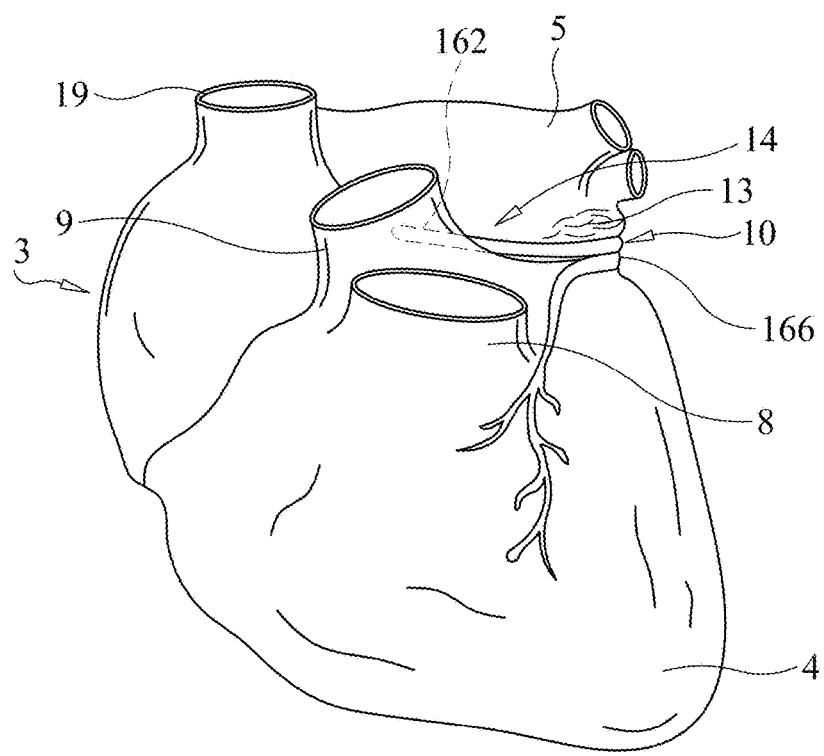
FIG. 4A is an anterior view of a human heart, with the device placed on the epicardial surface of the heart, according to an embodiment of the present invention.

For example, FIG. 4A is an anterior view of the heart 3, with the device 10 placed on the epicardial surface of the heart 3. As shown in FIG. 4A, the anterior segment 162 of the device 10 is positioned in the transverse sinus 14 posterior to the aorta 9 and the pulmonary trunk 8 and anterior to the left atrium 5 and the superior vena cava 19. The lateral segment 166 may extend around the left lateral side of the heart 3 at a location inferior to the left atrial appendage 13. In other embodiments, the lateral segment 166 may extend around the left lateral side of the heart 3 at a location superior to the left atrial appendage 13 or over the left atrium 5.

Figure 4B:
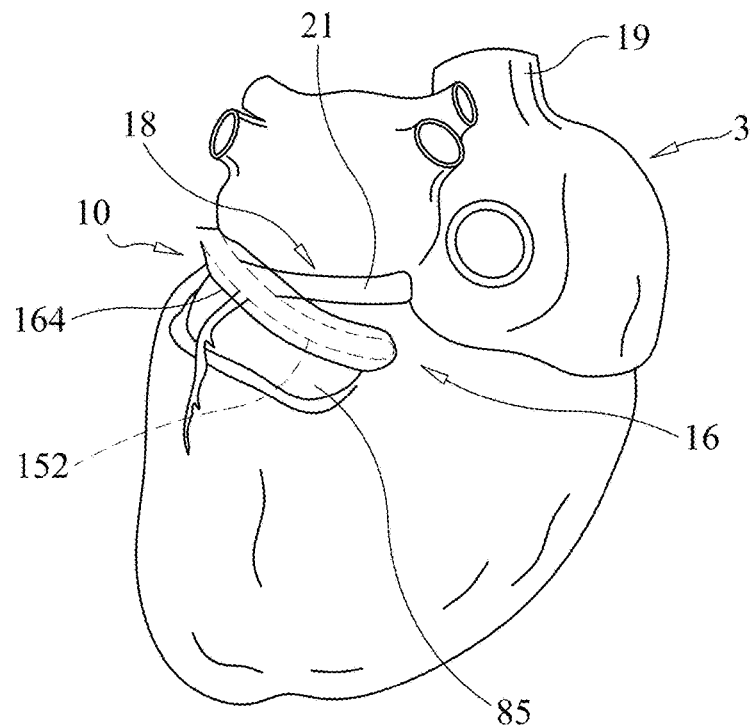
FIG. 4B is a posterior view of the heart shown in FIG. 4A with the device placed on the epicardial surface of the heart, according to an embodiment of the present invention.

FIG. 4B is a posterior view of the heart 3 with the device 10 placed on the epicardial surface of the heart 3. As shown in FIG. 4B, the posterior segment 164 of device 10 is positioned on the posterior of the heart 3 inferior of the atrioventricular groove 18. The posterior segment 164 may be positioned such that it is just below the circumflex artery 21. In other embodiments, the posterior segment 164 may be positioned such that it is just above the circumflex artery 21. Flap 85 extends inferiorly of the posterior segment 164 and is attached to foundation 185. Foundation 185 is anchored to the epicardial surface of the heart 3 in a position inferior of the posterior segment 164, at a target location that establishes an anchoring base to fix the flap 85 to secure the posterior segment 164 at the desired location, such as that shown in FIG. 4B.

Thus, the anterior segment 162 may be located in the transverse sinus 14. The posterior segment 164 may be positioned on the posterior side of the heart 3, such as on or inferior to the atrioventricular groove 18 or in the oblique sinus 16 and anchored in that position by fixing flap 85 to foundation 185. The position of the posterior segment 164 can be adjusted, if needed, by detaching the flap 85 from the foundation 185, repositioning the posterior segment 164 to a new location, and reattaching the flap 85 to the foundation 185, all without the need to remove any tacks, screws or other fixators from the heart. In some embodiments, the posterior segment 164 may be positioned inferior to the atrioventricular groove 18 on the posterior side of the heart 3. The lateral segment 166 may extend around the left lateral side of the heart 3 such that the anterior segment 162 is properly positioned in the transverse sinus 14 while the posterior segment 164 is properly positioned on the posterior side of the heart 3, such as on or inferior to the atrioventricular groove 18 or in the oblique sinus 16. In some embodiments, the lateral segment 166 may extend around the heart 3 at a location inferior to the left atrial appendage 13. However, in other embodiments the lateral segment 166 may extend around the heart 3 at a location superior to the left atrial appendage 13 or over the left atrium 5 to join the anterior segment 162 and the posterior segment 164. The anterior and posterior ends are spaced apart from one another by a predetermined distance and remain separated by a gap or opening after completion of implantation of the device 10.

The devices 10 of the present invention, when properly positioned, may reside on the epicardial surface of the heart 3, interior of the pericardium 15. Thus, positioning of the device 10 may not require penetration of the heart into one or more of the chambers of the heart and/or may not require the device 10 to come into contact with blood being located inside the chambers of the heart 3. By placing the device 10 on the epicardial surface, exterior of the interior of the heart 3, complications associated with surgical procedures in which access is required to one or more of the chambers of the heart 3 are avoided. By anchoring foundation 185 to the surface of the heart and anchoring the device 10 to the foundation 185 (via flap 85), the device 10 can be repositioned, removed or replaced without the need to remove any fixators from the surface of the heart 3, thereby making such procedures easier, faster and safer, as no bleeding from the heart wall will result from detachment of flap 85 from foundation 185 or from reattachment of a base 85 to foundation 185. Furthermore, the time required to complete the surgical procedure may be greatly reduced from the time required for an open heart surgery or a surgical procedure requiring accessing the heart 3 through the vasculature.

Figure 5:
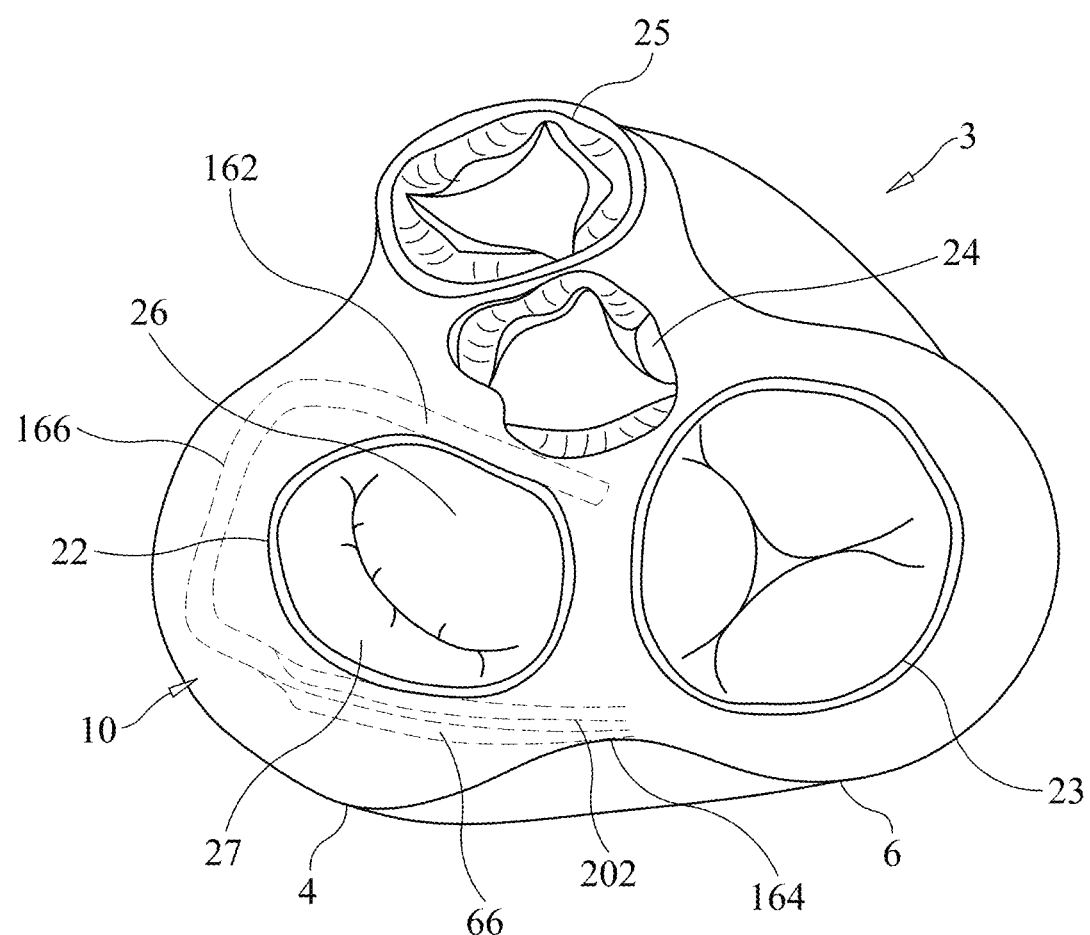
FIG. 5 is a top view of the ventricular portion of the heart with device shown in FIGS. 4A-4B, with the atria removed to shown the mitral valve.

FIG. 5 is a top view of the ventricular portion of the heart 3 with the atria removed. With the atria removed, the mitral valve 22 between the left atrium 5 (not shown in FIG. 5) and the left ventricle 4 is clearly shown. Also shown is the tricuspid valve 23 between the right atrium (not shown in FIG. 5) and the right ventricle 6, as well as the aortic valve 24 leading to the aorta 9 and the pulmonary valve 25 leading to the pulmonary trunk 8. As shown in FIG. 5, the mitral valve 22 includes two leaflets, an anterior leaflet 26 and a posterior leaflet 27. The mitral valve 22 is shown closed as it would be during systole. The device 10 is shown in phantom (dashed lines) in FIG. 5 as the device 10 may not lie in the plane of the mitral valve 22 shown.

When device 10 is properly placed around the heart 3 as illustrated in FIG. 5, the shape of the device 10 may reduce the anterior-posterior measurement of the mitral valve 22. In other words, the device 10 may urge the posterior leaflet 27 of the mitral valve 22 and anterior leaflet 26 toward one another, providing better contact (coaptation) of the anterior 26 and posterior 27 valve leaflets of the mitral valve 22, which may reduce or eliminate mitral regurgitation. Device 10 is manually adjustable in ways already described above to reposition the device 10 and particularly the posterior segment 164 (with possibly also some alteration in the position of segment 166) by detaching flap 85 from foundation 185, repositioning the device 10 to a desired position, and reattaching the flap 85 to the foundation 185. Thus, the placement of device 10 as shown in FIG. 5 can be installed in a manner to reduce or eliminate mitral valve regurgitation.

A method of treating mitral valve regurgitation as one preferred example of various methods of treatment that may be used to treat mitral valve regurgitation is now provided. In addition to variations of this method described, as well as variations in the particular device 10 used, it is further noted that the present devices are not limited to the treatment of mitral valve regurgitation, as they could be used to treat tricuspid valve regurgitation or regurgitation in another heart valve other than the mitral and tricuspid valves, and further could alternatively be used to treat any of the tissues/organs identified herein.

Figure 6A:
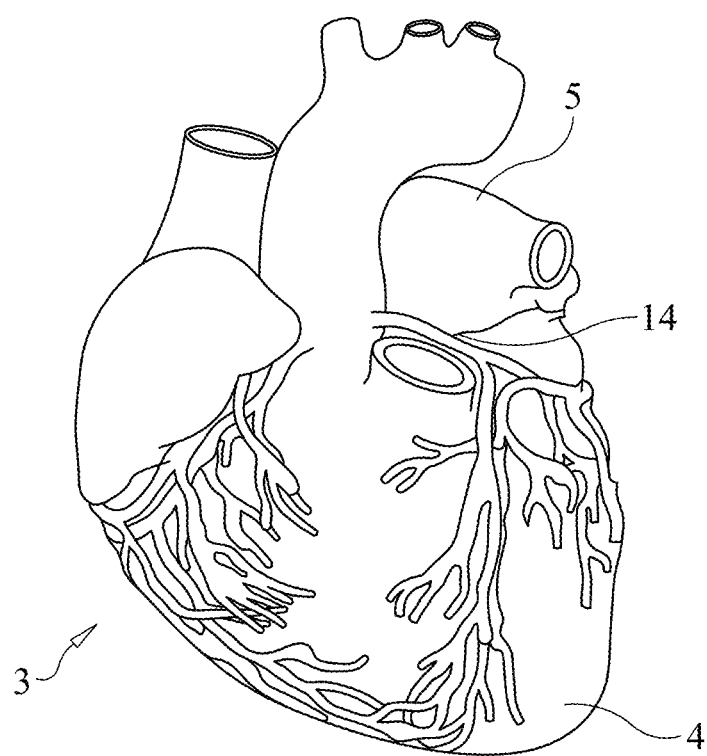
FIG. 6A. illustrates an anterior view of a human heart.

An exemplary, non-limiting embodiment of a procedure for installing the device/clip 10 of FIG. 1A is now described. In this embodiment, the heart 3 is exposed by way of an open chest procedure, via a sternotomy, according to known techniques. Upon opening the chest, an anterior view of the heart is directly visible to the surgeon. FIG. 6A illustrates an anterior view of the heart 3, with the left ventricle 4, left atrium and transverse sinus labeled. The posterior surface of the heart 3 (FIG. 6B), posterior surface of the ventricle 4, atrioventricular groove 18 and the oblique sinus 16 therefore cannot be seen directly by the eyes of the surgeon.

Figure 7A:
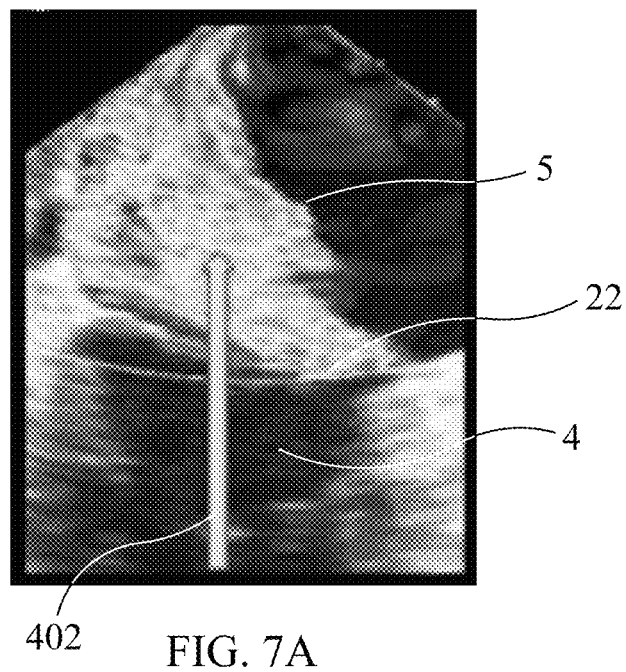
FIG. 7A shows an echocardiogram illustrating occurrence of severe mitral valve regurgitation during systole.
Figure 7B:
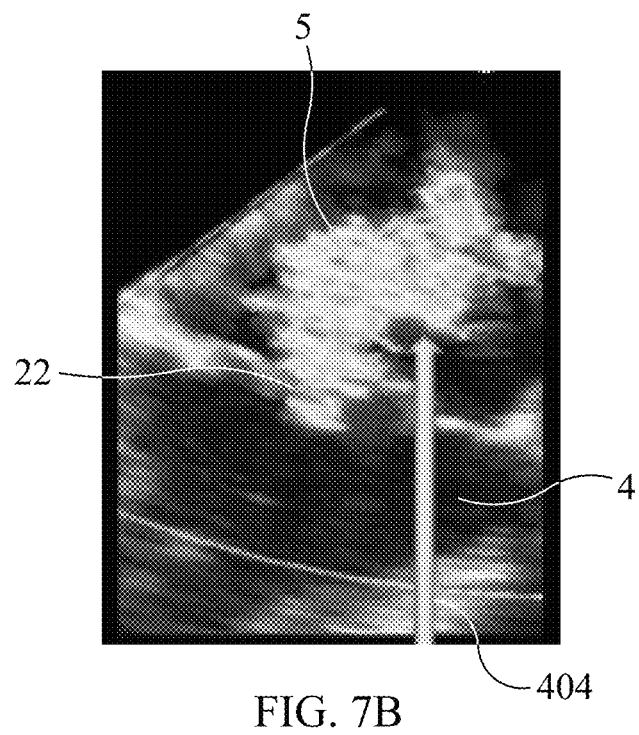
FIG. 7B shows an echocardiogram illustrating occurrence of moderate mitral valve regurgitation during systole.
Figure 7C:
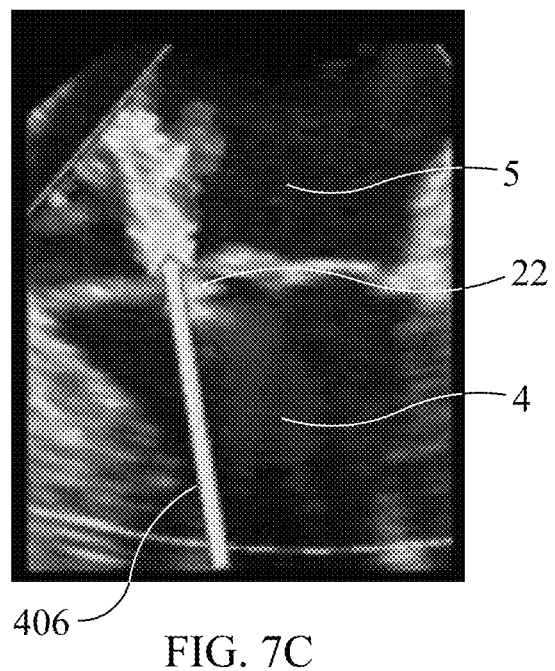
FIG. 7C shows an echocardiogram illustrating occurrence of mild mitral valve regurgitation during systole.
Figure 7D:
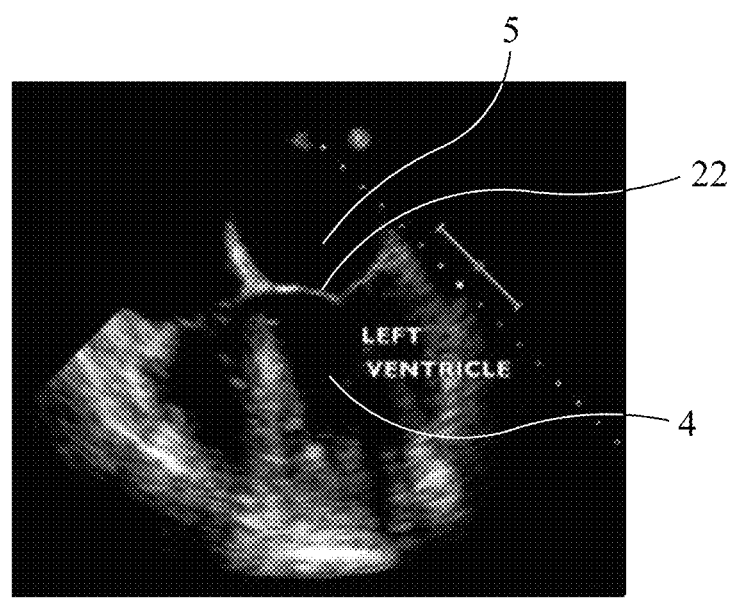
FIG. 7D shows an echocardiogram where no mitral valve regurgitation occurs during ventricular systole.

Visualization of the blood flow through the mitral valve 22 can be provided by echocardiography, for example to identify mitral valve regurgitation that may be occurring. The echocardiography provides images that show blood flowing from the left atrium 5 through the mitral valve 22 and into the left ventricle 4 (atrial systole) and also provides images that can identify when blood flows retrograde from the ventricle 4 through the mitral valve 22 and into the left atrium 5, a malady that typically occurs during ventricular systole. Ultrasound energy is applied to the heart 3 in the area of the left ventricle 4, mitral valve 22 and left atrium 5 to provide images that are transverse to the plane of the mitral valve annulus, which may or may not be normal to the plane, but are typically near to normal. However, other angles of visualization may also be used. FIG. 7A shows an echocardiogram illustrating occurrence of severe mitral valve regurgitation, where a large, brightly colored plume 402 indicates the retrograde blood flow through the mitral valve, thus indicating the large volume of regurgitation of blood from the ventricle that is occurring during ventricular systole. FIG. 7B shows an echocardiogram illustrating occurrence of moderate mitral valve regurgitation where plume 404 is somewhat smaller than plume 402 and less brightly colored overall, indicating that the amount of retrograde blood flow through the mitral valve 22 during ventricular systole is less than that shown in FIG. 7A. FIG. 7C shows an echocardiogram illustrating occurrence of mild mitral valve regurgitation 402 during ventricular systole, wherein plume 406 is clearly much smaller than 402 and much smaller than 404. FIG. 7D shows an echocardiogram where no mitral valve regurgitation occurs during ventricular systole, as it can be seen that the left atrium is dark in this echocardiogram. By providing real time echocardiography as described, the surgeon/surgical team can visually ascertain the amount of mitral valve regurgitation as the heart 3 is manipulated in an effort to find a condition where reduction, minimization or elimination of mitral valve regurgitation can be achieved.

Figure 6B:
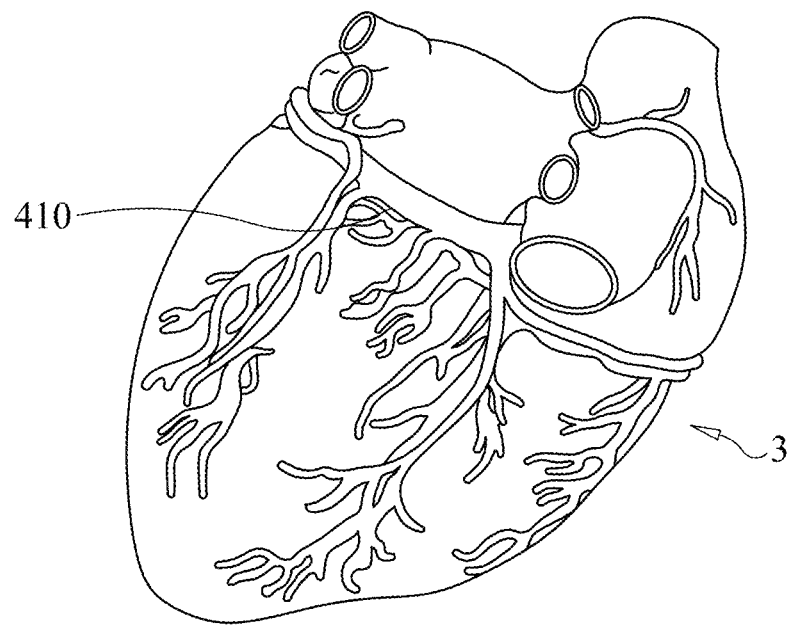
FIG. 6B illustrates a posterior view of the heart of FIG. 6A.

To perform such manipulation, force is applied posteriorly to the heart 3 on or inferior to the atrioventricular groove 18 or in the oblique sinus 16, in a location where the posterior segment 164 is intended to contact the heart 3 upon implantation of the device/clip 10. FIG. 6B indicates the general location 410 where the force is applied. Note that because FIG. 6B is a posterior view of the heart 3, the surgeon cannot see where the force is being applied, but it needs to be applied through feel to locate the appropriate location to apply the force. The amount of force and/or location of application of force applied may be varied while viewing the echocardiographs provided in real time on a monitor until a location and amount of force are applied that achieve a result of reduction, minimization or elimination of mitral valve regurgitation.

Figure 8:
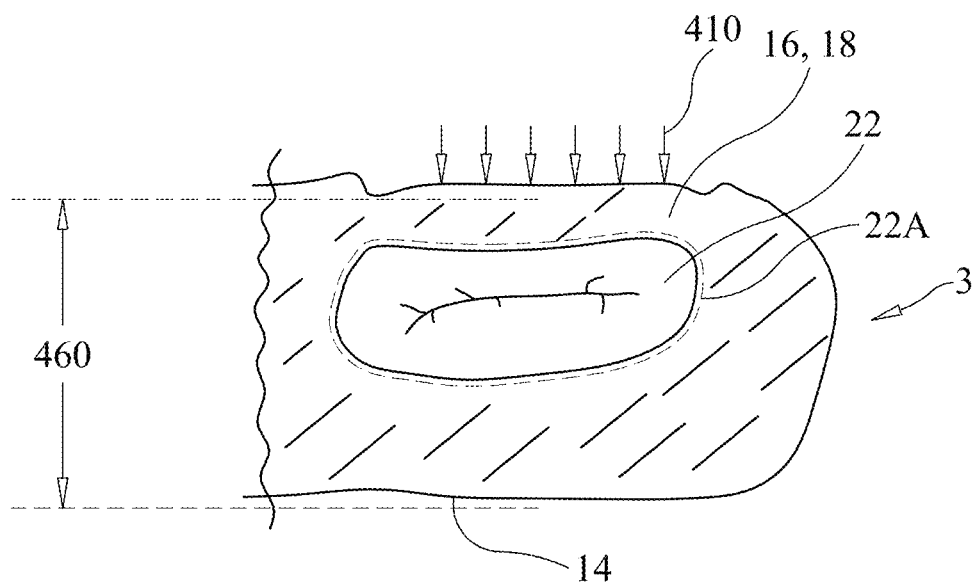
FIG. 8 illustrates an echocardiogram taken in a plane (or approximating a plane) of the mitral valve annulus, according to an embodiment of the present invention.

When the location and amount of force applied for achieving a result of reduction, minimization or elimination of mitral valve regurgitation are established, an echocardiogram taken in a plane (or approximating a plane) of the mitral valve annulus is provided, a schematic illustration of which is shown in FIG. 8. A measurement of distance 460 between the epicardial surface of the posterior heart 3 wall and the epicardial surface of the anterior heart wall in the transverse sinus 14, at locations corresponding to locations of distance 160 measured in FIG. 1A, on the heart 3 where those locations of the device/clip 10 are intended to be located, provides a measurement 460 that can be used to select a device clip 10, wherein measurement 160 of device clip 10 is equal to measurement 460 (or nearest to measurement 460, as selected from a kit of device clips 10 having different measurement distances 160.

Figure 9:
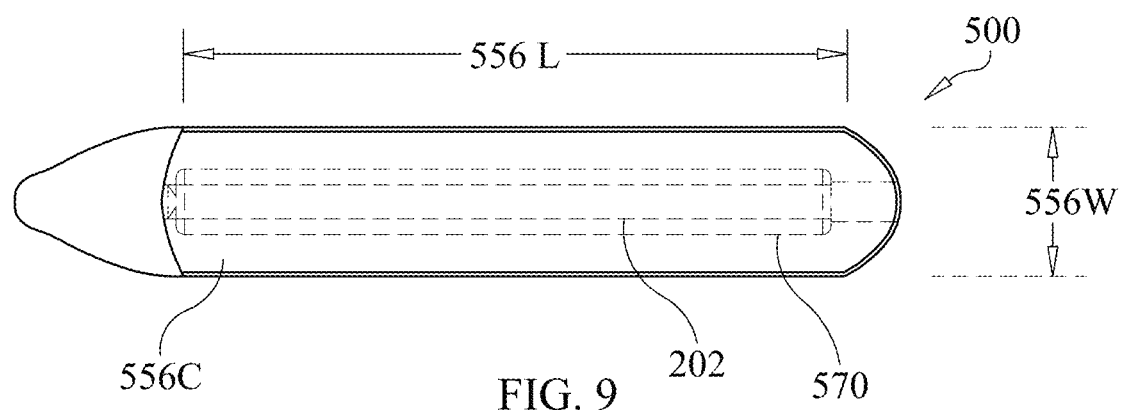
FIG. 9 is a view of a width sizing instrument with a view of the contact surface, according to an embodiment of the present invention.

FIG. 9 is a view of a width sizing instrument 500 with a view of the contact surface 556c according to an embodiment of the present invention. The width 556W and length 556L are preferably the same or nearly the same as the width 56W and length 56L of the contact surface 56 of device/clip 10 that is intended to be implanted, in order to provide a close simulation of the manner in which force will be applied through the contact surface 56 to the heart 3. Likewise, it is preferred that the curvature and conformation of the contact surface 556c be the same, or closely matching that of the curvature of contact surface 56c. At least the contact component 556 may be made from the same material as the pad 56. However, because silicone is not highly visible under echocardiography, it may be preferable to include one or more contrast agents such as air bubbles encapsulated in the contact component material, low solubility fluorocarbon gas, polymer shell and low solubility gas, or other contrast materials known in the art. Further optionally, a rod/rib 202 having the same characteristics (makeup, dimension, shape, etc.) of rod/rib 202 of the device 10 may be included as shown. Length 556L may be in a range from 25 mm to 70 mm, 30 mm to 60 mm, 40 mm to 50 mm, or 42 mm to 48 mm, for example. In one particular embodiment, length 556L was 45 mm. Width 556W may be in a range from 5 mm to 30 mm, 10 mm to 25 mm, 12 mm to 20 mm, or 13 mm to 17 mm, for example. In one particular embodiment, width 556W was 15 mm. Additional embodiments of width sizing instruments that can be used in place of the width sizing instrument 500 of FIG. 9 are disclosed in co-pending International Application Serial No. PCT/US2019/015300, titled "Epicardial Valve Repair System", filed concurrently herewith and incorporated herein, in its entirety, by reference thereto.

Figure 10:
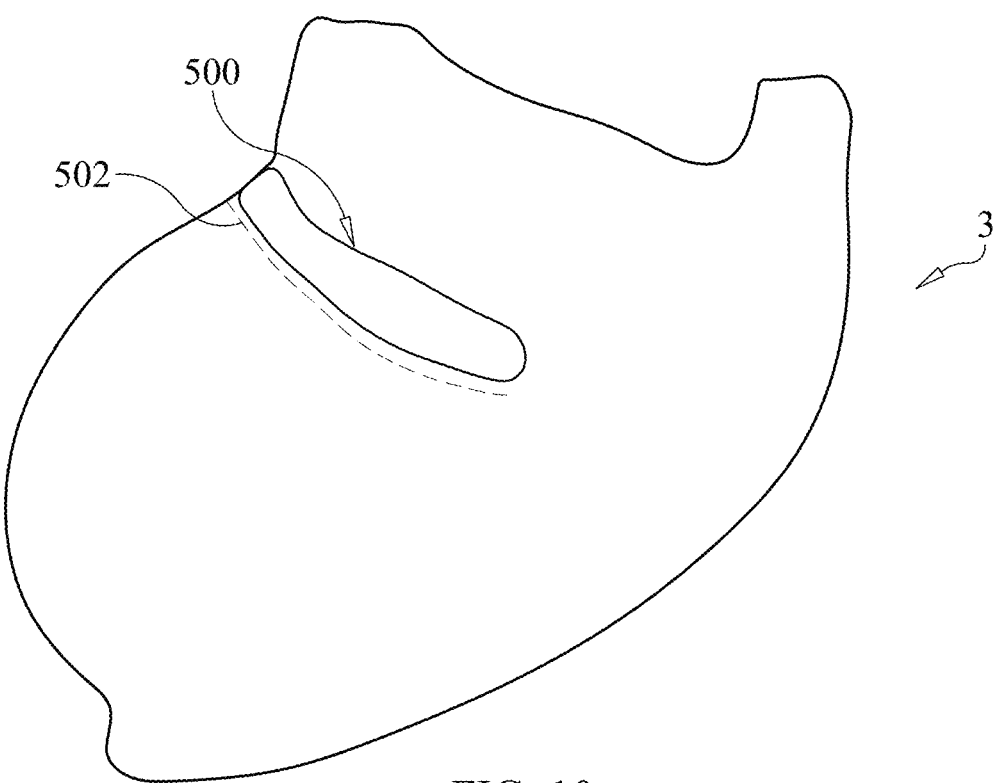
FIG. 10 is a schematic illustration of application of force through a width sizing instrument to the posterior surface of the heart, according to an embodiment of the present invention.

FIG. 10 is a schematic illustration of application of force through width sizing instrument 500 to the posterior surface of the heart 3. As noted, this part of the procedure is performed with the heart 3 in the chest of the patient, in a position as close to its natural position as possible to achieve the best measurement and positioning results. As the view illustrated in FIG. 10 is not visible to the surgeon, this placement is done by feel, using feedback provided by echocardiography. When the location and amount of force applied for achieving a result of reduction, minimization or elimination of mitral valve regurgitation are established, the posterior surface of the heart 3 is marked to indicate where the placement of the sizing instrument 500 is currently established, as this will also establish the position where the sizing instrument 500 is placed as the target location in which the posterior segment 164/pad 56 is to be placed. Marking may be performed using a surgical marker or some other type of biological ink applicator, or other biological marker, including, but not limited to those described in Provisional Application Ser. No. 62/622,830, which is incorporated herein, in its entirety. For example, width sizing instrument 500 may be configured to perform the marking. As shown the mark is made inferiorly adjacent to the inferior edge of the sizing instrument 500. Additionally or alternatively, marking may be performed at any other location defined by an established distance and orientation to a reference location of the posterior segment 164 that is to be placed.

Figure 11:
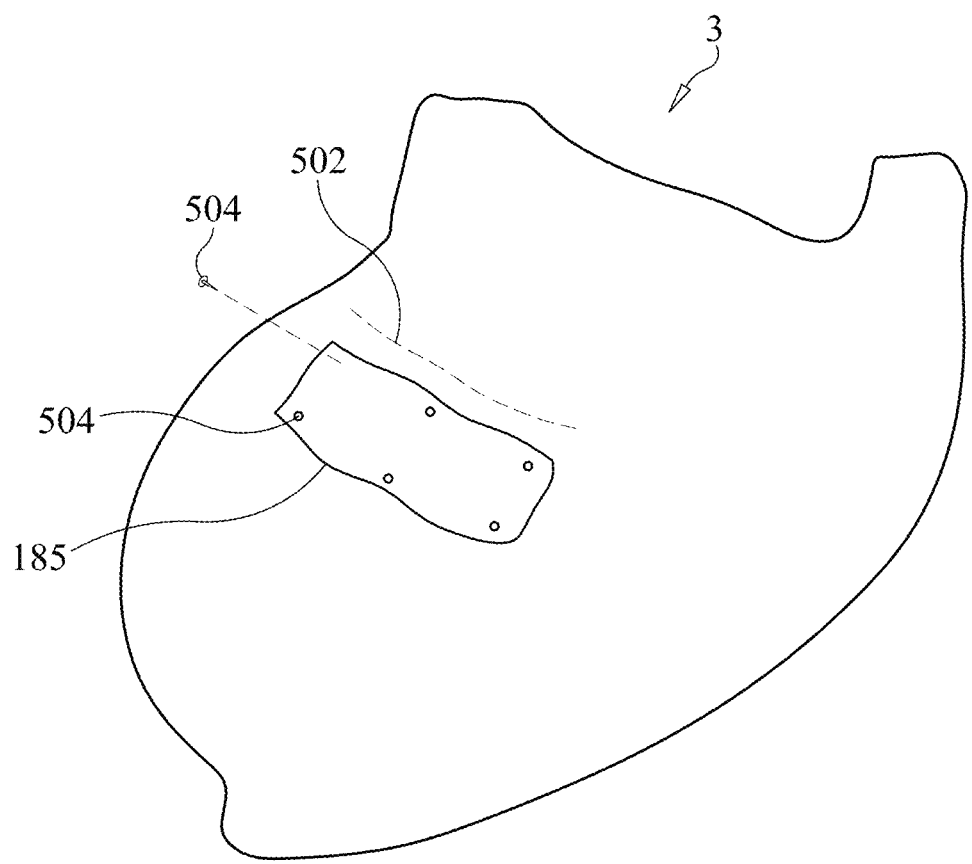
FIG. 11 is a schematic illustration of anchoring a foundation to the epicardial wall of the posterior side of the heart, according to an embodiment of the present invention.

Once the target position that the posterior segment is to occupy on the heart 3 has been established as described, the sizing instrument 500 is removed and the heart 3 is lifted at least partially out of the chest cavity so that the surgeon can directly view the target position and marking 502. Foundation 185 is next anchored to the epicardial wall of the posterior side of the heart 3, using fixators 504, such as tacks, screws, or equivalent, as illustrated in FIG. 11. The positioning of the foundation 185 is relative to the marking 502, typically aligned therewith, where the superior edge of the foundation 185 can be placed immediately adjacent to or parallel to but spaced by a predetermined distance from the marking 502. Other variations of the relationship of the positioning of the foundation 185 relative to the marking 502 may exist, such as when the marking 502 is placed at a location other than along the inferior edge of the sizing instrument 500.

Figure 12:
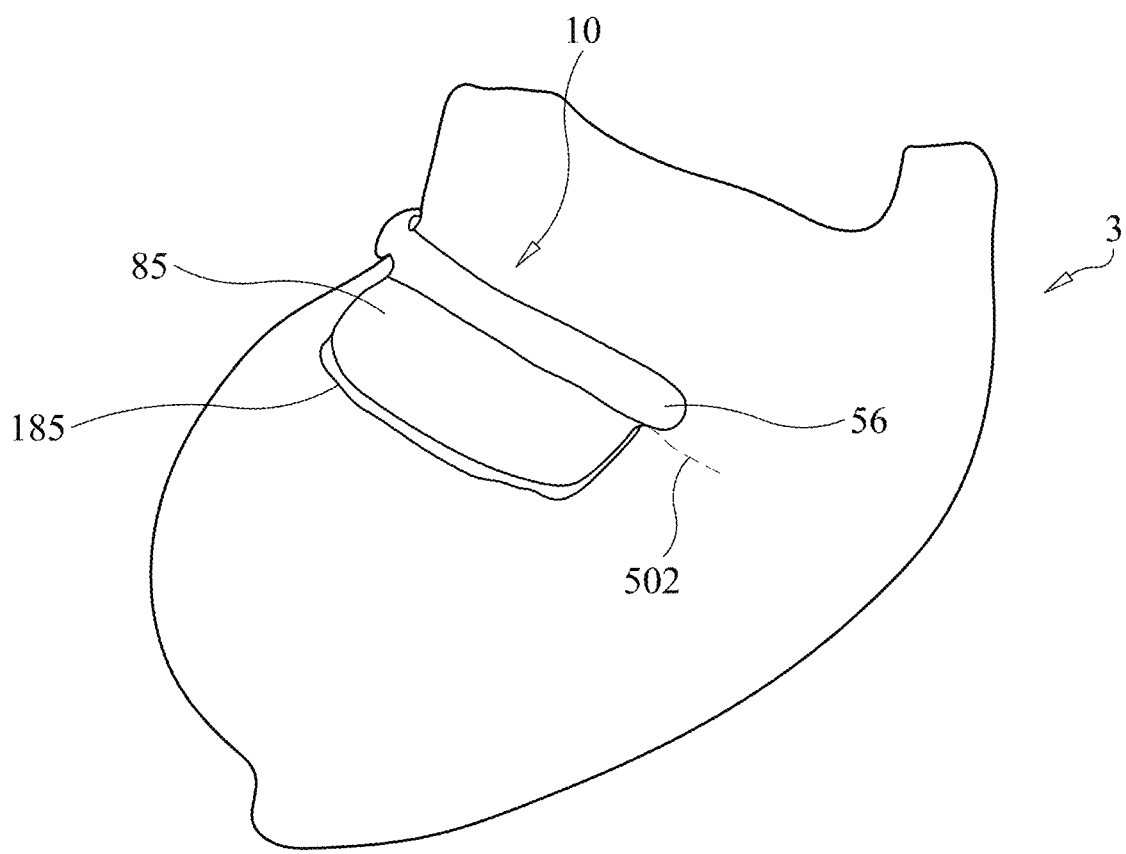
FIG. 12 illustrates the device clip having been installed on the heart, and the flap having been attached to the foundation, according to an embodiment of the present invention.

Device 10 can next be fixed to the epicardium of the heart 3. The anterior segment 162 is inserted into the transverse sinus, and the lateral segment 166 wraps around so that the posterior segment can be positioned in alignment with the marking 502. In the embodiment shown in FIG. 12, the inferior edge of the pad 56 of posterior segment 164 is aligned with the marking 502. To maintain this position, flap 85 is attached to foundation 185 as shown. Optionally the anterior segment may be placed in a sleeve in the transverse sinus and the sleeve can be anchored to the transverse sinus with tacks, screws or other fixators. After fixing the device 10 to the heart 3 as described, the heart 3 can then be lowered back into its natural position in the chest cavity. Additional echocardiography can be performed in the manner described above with regard to FIGS. 7A-7D to determine the amount of reduction of MR regurgitation that has been accomplished. At this time it is possible to adjust the device 10, and particularly the posterior segment 164, if needed to improve the results. This adjustment can be accomplished either in the chest cavity, or the heart can again be lifted and rotated to perform the adjustment under direct visualization. Adjustment in the chest cavity is preferred, as it requires less time and manipulation, and can be readily performed by feel, as the surgeon can detach the flap 85 from the foundation, reposition the posterior segment 164, and reattach the flap 85 to the foundation without the need to directly visualize any of these steps. The adjustment steps can be iterated as many times as needed to optimize the reduction, minimization or elimination of mitral valve regurgitation. When the device 10 position has been optimized, the patient can be closed according to standard procedures and the flap 85 remains fixed to the foundation 185 to maintain the device 10 in the optimized position and orientation. Advantageously, the present invention allows a subsequent procedure to be carried out in the future, should it become necessary to adjust the position of the device 10 or remove the device 10 for any reason, including, but not limited to replacing it with a different sized device 10. Any such additional procedure can be carried out without the need to remove the foundation 185 and therefore bleeding of the heart wall from removing fixators can be avoided.

Figure 13:
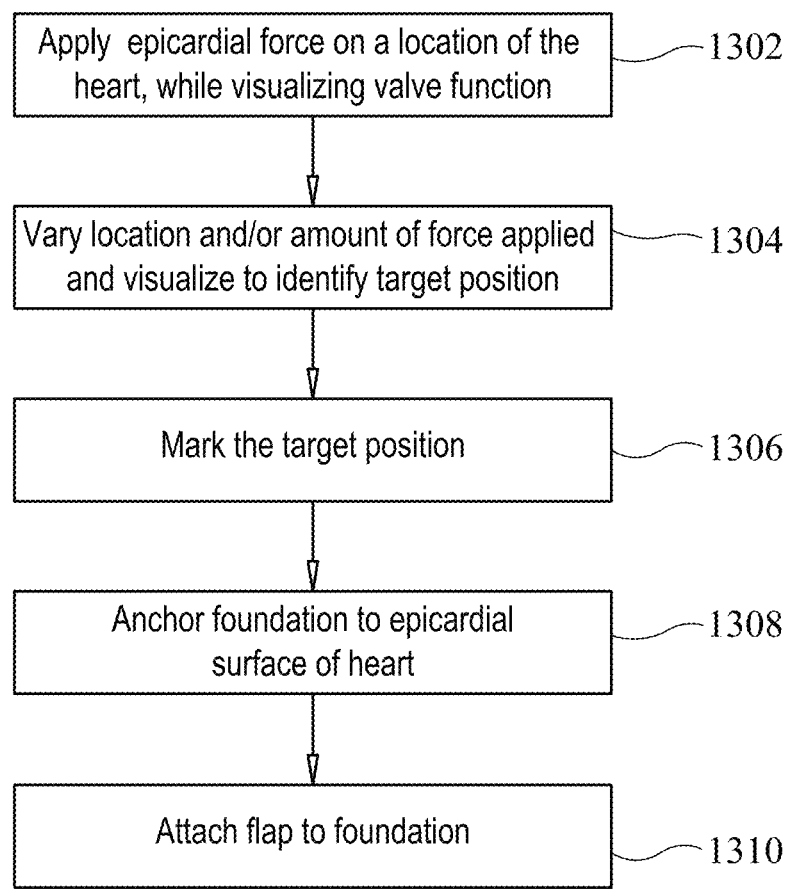
FIG. 13 illustrates a number of events that can be carried out in a method of implanting a device according to an embodiment of the present invention.

FIG. 13 illustrates a number of events that can be carried out in a method of implanting a device according to an embodiment of the present invention. After establishing an opening in the patient to provide access to the heart (which can be open-chest, a lateral thoracotomy, or endoscopic, as noted above, or other opening allowing access), an epicardial force is applied on a location of the heart, while visualizing regurgitation through the valve via visualization apparatus at event 1302. As noted above the force is typically applied to a posterior location of the heart adjacent the valve to be treated. The location of the application of force and/or the amount of force applied can be varied, while continuing the visualization, at event 1304, until a combination of a location and amount of applied force is found where visualization confirms that valve regurgitation is reduced, minimized or eliminated to the satisfaction of the surgeon. The location of the application of force where it is found that the valve regurgitation is reduced, minimized or eliminated as described is considered to be the target location for application of force by a device to be implanted/installed, and the target position is marked at event 1306 according to any of the marking methods previously described.

At event 1308, a foundation is anchored to the epicardial surface of the heart to provide a base for fixing an epicardial device thereto. The foundation is fixed according to a predetermined relationship to the marked location so that attachment of the flap to the foundation will result in the posterior segment of the device being located at the target location. At event 1310, the device 10 is fixed by attaching flap 85 to the foundation 185. This establishes a segment of the device in the target position and indirectly fixes the epicardial device to the heart 3 via the foundation 185.

To confirm that the device 10 has been properly placed for performance as desired, further visualization of the functioning of the valve may be carried out after the attachment event of 1310. If it is seen that a greater amount of regurgitation is recurring than what was occurring during visualization at the time that the target location was identified, then the surgeon may choose to detach the flap 85 from the foundation, reposition the epicardial device 10 to reduce the amount of regurgitation and verify reduction in regurgitation by further visualizing. The flap 85 is reattached to the foundation 185 and further verification can be performed using the visualization.

Any of the methods described herein may optionally further include measuring the distance between the target location when the force is applied and the epicardial surface of the heart wall opposite the target location, and using the measurement for selecting a device having distance 160 that best matches the measured distance, such as described above with regard to FIG. 8.

Further optionally, it may be desirable to perform a length measuring procedure to establish an optimum length or length range for the length 162L of the anterior segment 162 of the device/clip 10 that is to be used for the procedure. An optimal length 162L of the anterior segment 162 is one which extends as far as possible into the transverse sinus 14, without obstructing or potentially causing any damage to any structures that may lie in the path of the transverse sinus 14. This provides the greatest amount of securement of the clip/device 10 by the anterior segment portion 162 without unduly risking damage or trauma to the surrounding tissues. Because the occurrence or existence of one or more structures (such as a pulmonary vein or other vessel or structure) lying in the path of the transverse sinus 14 can vary from patient to patient, and because it is not possible to directly view such occurrences, it may be advantageous to perform a length measurement of the transverse sinus 14, to the extent that it is unobstructed, to determine the maximum length of anterior segment 162 of a clip/device 10 that can be safely used on a particular patient.

Figure 14A:
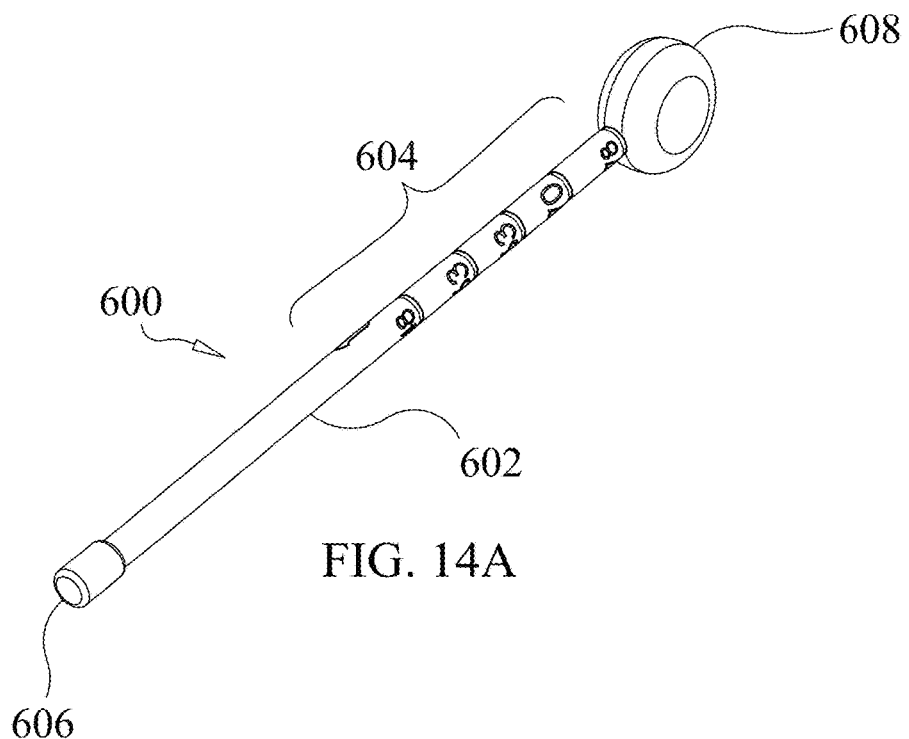
FIGS. 14A-14C are perspective and plan views of a length sizing instrument, according to an embodiment of the present invention.
Figure 14B:
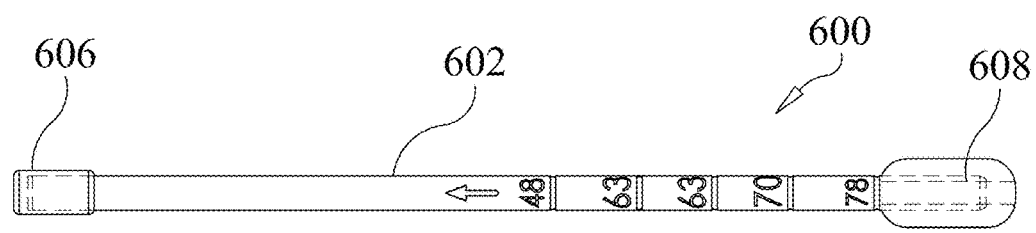
Figure 14C:
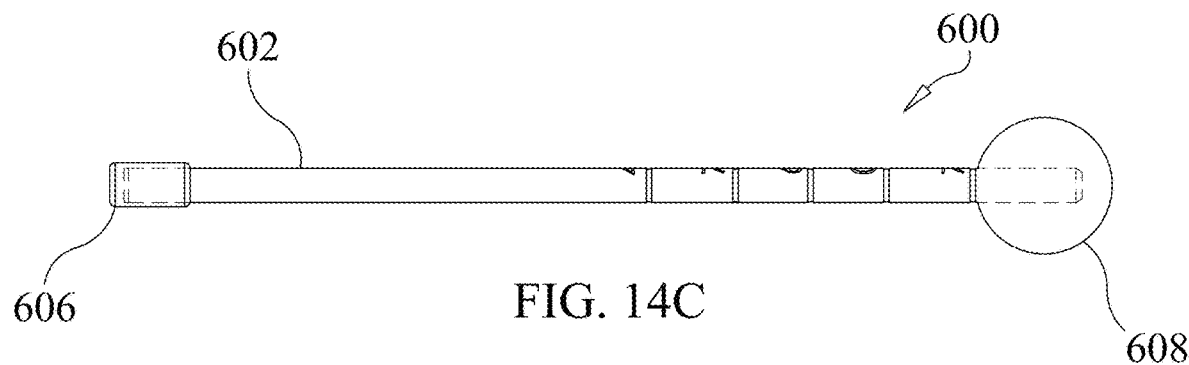

FIG. 14A is a perspective view, FIG. 14B is a plan view, and FIG. 14C is another plan view (rotated ninety degrees about the longitudinal axis of the view of FIG. 14B) of a length sizing instrument 600 according to an embodiment of the present invention. Instrument 600 includes a shaft 602 as the main body of the instrument. Shaft 602 is preferably a straight shaft and preferably has the same diameter as the diameter of the rod 202 used in making the anterior segment 162 of device/clip 10. However, the diameter of 602 may be smaller, or even slightly larger than the rod 202 and still function. Graduated markings 604 are provided along the shaft 602 to be referenced for making measurements of the unobstructed transverse sinus 14. An atraumatic tip 606 may be formed at a distal end of the shaft 602 to prevent damage to tissues within the transverse sinus 14 (such as obstructions, or the walls of the tissue forming the transverse sinus) as the instrument 600 is being inserted into and advanced along the transverse sinus 14. An enlargement 608 may be formed at the proximal end of the shaft 602 to function as a handle, facilitating the operation and manipulation of the instrument 600 by a user. In a preferred embodiment the instrument 600 is formed of the same materials used to make a device/clip of the present invention. For example, shaft 602 in one specific embodiment has a titanium shaft, and the atraumatic tip 606 and handle 608 are over-molds of silicone on the shaft 602. In another embodiment, atraumatic tip 606 and handle 608 are configured to form a friction fit with the shaft 602, such as by making the openings of the handle 608 and tip 606 of a smaller inside diameter than is the outside diameter of the shaft 602. In one particular non-limiting embodiment, these inside diameters were 0.381 mm less than the 3.175 mm outside diameter of shaft 602. Additional embodiments of length sizing instruments that can be used in place of the length sizing instrument 600 of FIGS. 14A-14C are disclosed in co-pending International Application Serial No. PCT/US2019/015300, titled "Epicardial Valve Repair System", filed concurrently herewith and incorporated herein, in its entirety, by reference thereto.

Figure 15:
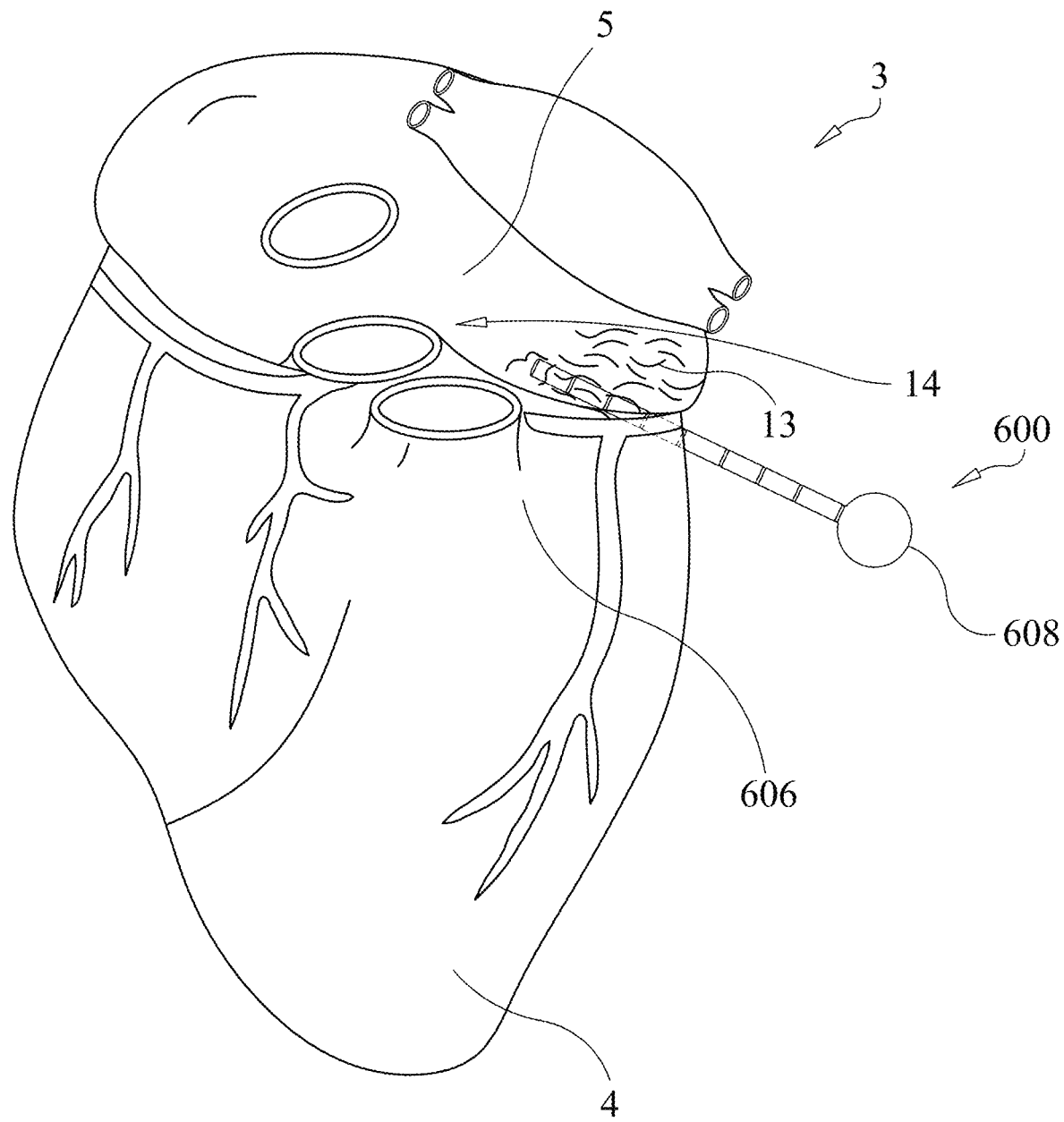
FIG. 15 illustrates insertion of a length sizing device into the transverse sinus of a heart of a patient to be treated for mitral valve regurgitation, according to an embodiment of the present invention.

FIG. 15 illustrates insertion of a length sizing device 600 into the transverse sinus 14 of a heart 3 of a patient to be treated for mitral valve regurgitation. The user typically grips the instrument 600 via handle 608 and gently inserts the atraumatic tip 606 of the instrument through the opening of the transverse sinus 14. While carefully advancing the tip 606/instrument 600 into the transverse sinus 14, pressure may be applied against the shaft 602 toward the heart wall so as to keep the shaft 602 as far against the wall and the interior wall of the transverse sinus 14 as practical, as this will be the most secure location for the anterior segment 162. The instrument 162 is advanced until the end of the transverse sinus 14 is abutted by the atraumatic tip 606 or until the atraumatic tip abuts a structure that extends into the transverse sinus or until the atraumatic tip abuts an abrupt turn in the transverse sinus 14 that occurs about when transverse sinus approaches the right atrium. At this time, the graduated scale 600 is read by the user to measure the usable length of the transverse sinus. For example, if the graduated scale reads 55 mm at the opening of the transverse sinus, then a device clip 10 having the longest anterior segment that is not greater than 55 mm would be selected for use in this case. Thus, if devices 10 having anterior segment 162 lengths of 45 mm, 53 mm and 63 mm and 70 mm were available for selection, the device having the anterior segment length 162L of 53 mm would be selected for use in this case.

Once a preferred size (width 160 and length 162L) of device 10 has been selected, the anterior segment 162 can be inserted into the transverse sinus 14 and the posterior segment 164 can be positioned in the correct location on the posterior wall of the heart 3 identified during the width sizing procedure, and the posterior segment can be anchored to the position by attaching flap 85 to foundation 185, as described above. Optionally, the anterior segment 162 may also be anchored in the transverse sinus using tissue anchors, tacks or the like, inserted through a sleeve or a flap extending from the anterior segment 162.

Figure 16A:
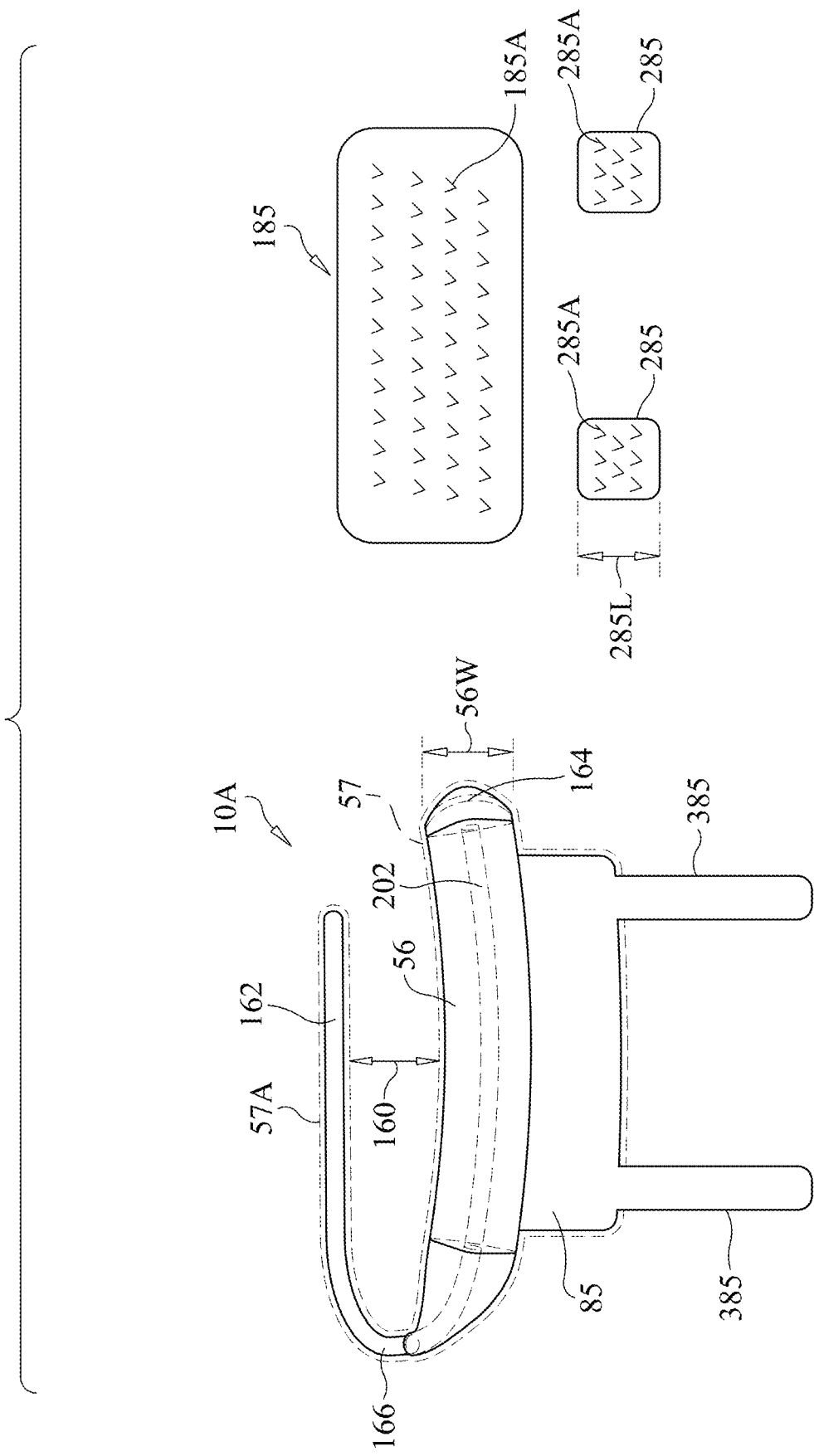
FIG. 16A is a posterior, perspective view of an epicardially implantable device according to another embodiment of the present invention.

FIG. 16A is a posterior, perspective view of an epicardially implantable device 10A according to another embodiment of the present invention. In this embodiment, device 10A may have any of the same characteristics of device 10 described above with regard to FIG. 1A, in addition to the features now described. In this embodiment, at least one additional foundation 285 is provided, in addition to the foundation 185. Although two additional foundations 285 are shown, alternatively only one or more than two additional foundations may be provided, with an equal number of extensions 385 to be attached thereto.

Figure 17:
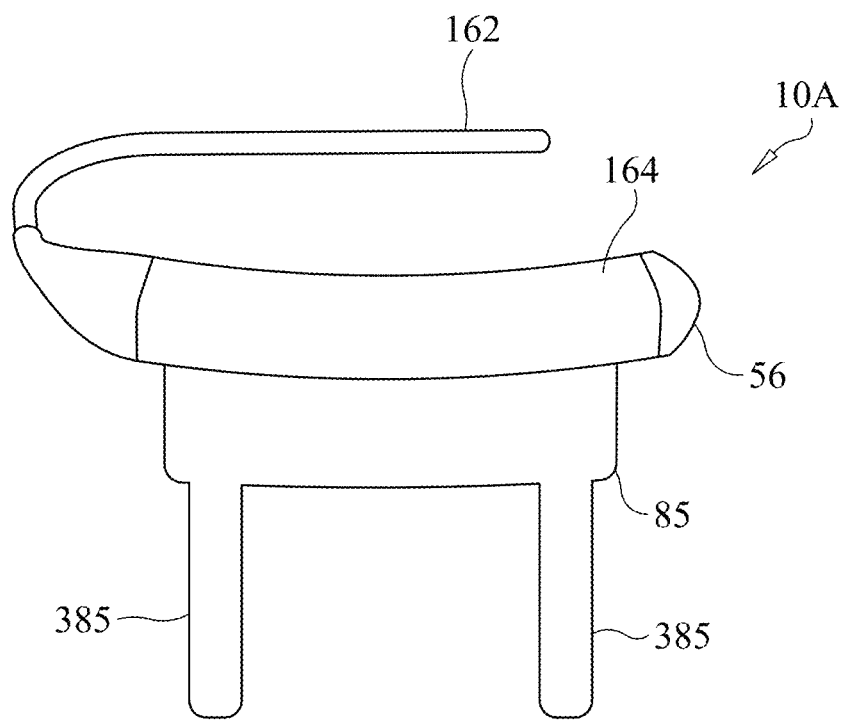
FIG. 17 is a variant of the device of FIG. 16A.

Extensions 385 extend inferiorly from the flap 85 or from pad 56 (FIG. 17) or alternatively may extend from sheath 57 if employed, or, if the pad 56 is not included, the main frame 202 of the posterior segment 164. Extensions 385 may be made of any of the same materials descried for making flap 85. Extensions 285 typically extend inferiorly from the flap 85 by a distance in the range from 0.5 cm to 3 cm, preferably from about 1 cm to 2 cm. Extensions 385, when attached to foundations 285, function to apply compressive force between foundation 285 and foundation 185 and/or posterior segment 164, which causes a reduction in tension on the chordae tendineae thereby facilitating better coaptation of the valve leaflets that the chordae tendineae are attached to, as described in more detail below.

Foundation(s) 285, like foundation 185 is/are separately provided and is/are configured to be implanted to the surface of the heart, such as by anchoring using tacks, screws or other equivalent fixation means. Foundation 285 is a thin structure that can be fixed to the heart wall prior to anchoring the posterior segment 164. For example, foundation 285 may be made from a thin layer of silicone or other structural core layer to provide structure thereto, which may then be covered with any of the same materials described above for use in making sheath 57. Alternative materials could be used that are biocompatible and flexible, but which have sufficient rigidity to provide structural support to the foundation, such that it can be deformed to conform to the curvature of the surface of the heart that it is being anchored to, but retains sufficient rigidity so that it does not buckle, wrinkle, or otherwise deform from its conforming shape. Optionally that core of the foundation may not be covered. For example, once the target location for fixation of the posterior segment 164 is identified the one or more foundations 285 can be fixed at positions that are located by a predetermined distance inferior to the target location. For example, the predetermined distance may be determined by a typical distance that the papillary muscles and chordae tendineae extend from the valve leaflets (when closed) to the location on the internal wall of the heart where the chordae tendineae attach. The predetermined distance may be about the same as this typical distance or slightly less, or slightly greater, preferably slightly greater. The predetermined distance may be in a range from about 2 cm to about 10 cm, typically from about 4 cm to about 8 cm or from about 5 cm to 7 cm. Using the embodiments of FIG. 16A or 17, the foundation 185 can be implanted on the heart wall in a location that will fix the posterior segment in the target location when flap 85 is attached to foundation 185 and the foundations 285 can be implanted on the heart wall at predetermined distances from the target location of the posterior segment 164 so that, extensions 385 can be attached thereto under tension, to apply compression force between anchors 285 and posterior segment 164 and/or anchor 185.

Figure 16B:
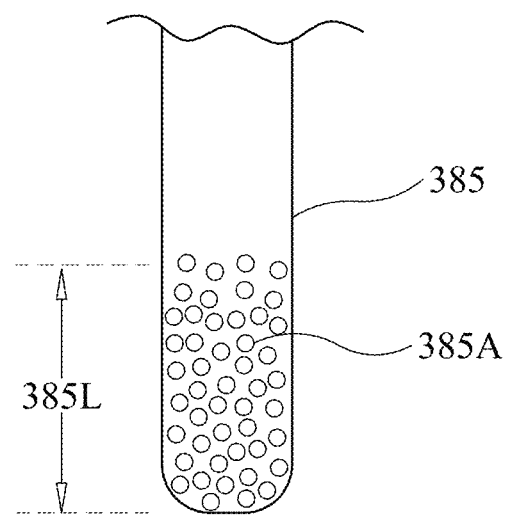
FIG. 16B is an isolated view of anterior surface of an extension of the device of FIG. 16A.

To establish the attachment of extension 385 to foundation 285, the surfaces of the extension 385 (see isolated view of anterior surface of extension 385 in FIG. 16B) and foundation 285 that come into contact with one another to accomplish the attachment are provided with mating attachment features 285A, 385A. The attachment features 285A, 385A may be the same as any of those described above for attachment features 85A, 185A. The surface area of the outer surface of foundation 285 may be equal to, less than or greater than the surface area of the surface of extension 385 that it interfaces with. Preferably, the attachment features 385A may extend along a length portion 385L that is greater than the length 285L of foundation 285 to allow greater adjustability of the attachment of extension 385 to foundation 285 for varying the amount of tension applied.

Figure 18:
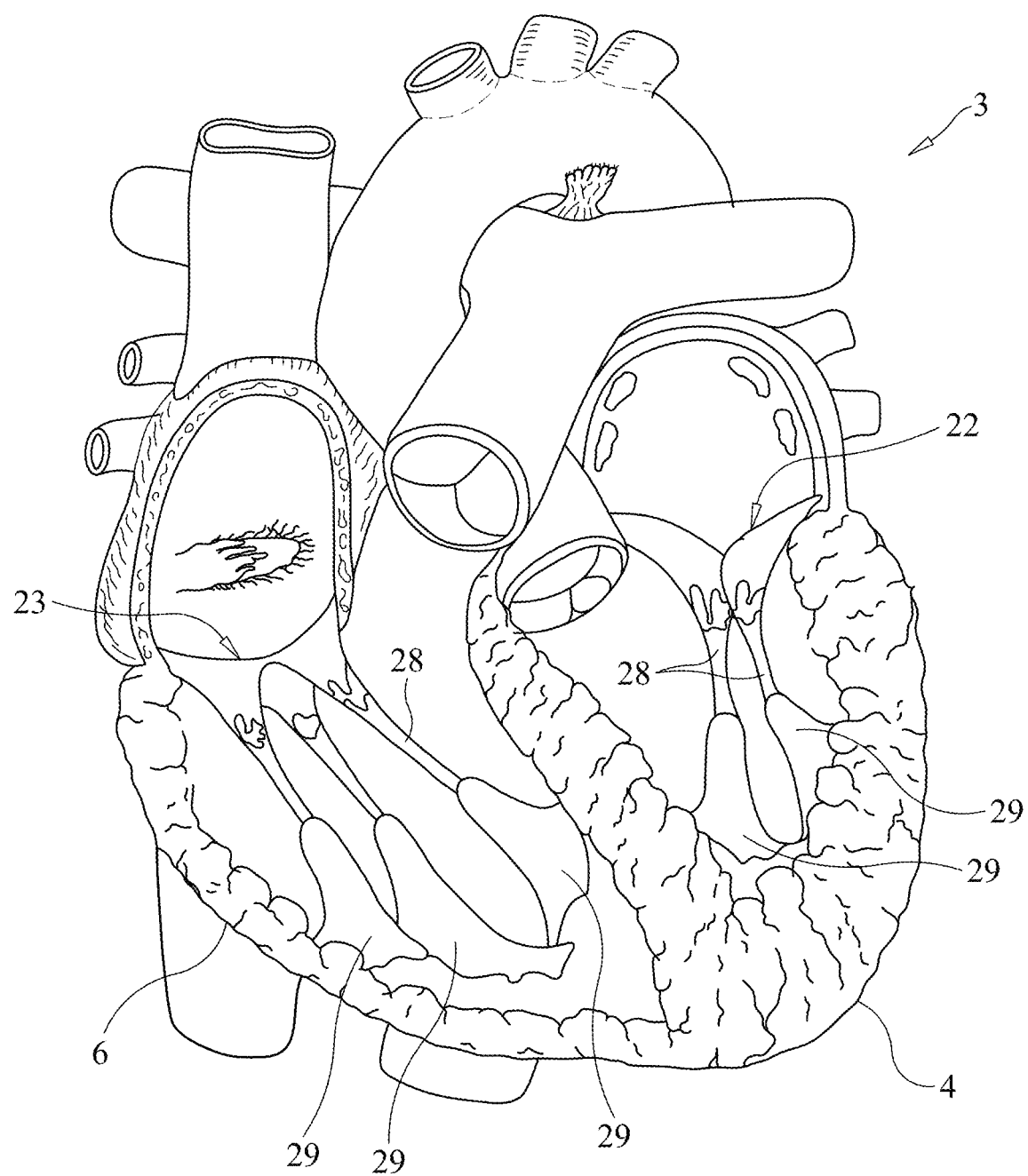
FIG. 18 is a cutaway view of a human heart illustrating chordae tendineae and papillary muscles in the left and right ventricles.
Figure 19:
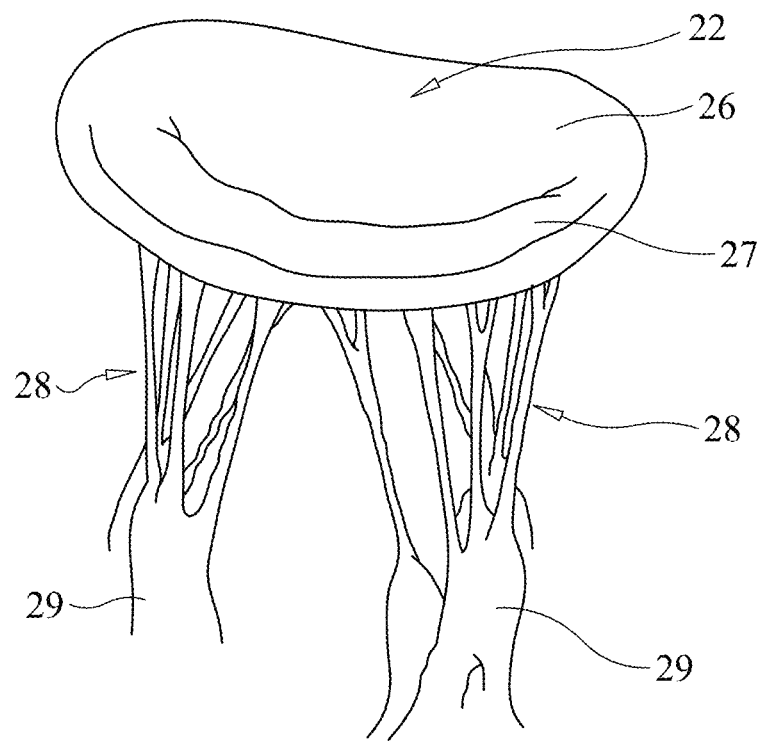
FIG. 19 is an isolated view showing attachment of the papillary muscles to the anterior leaflet and posterior leaflet of the mitral valve via chordae tendineae.

FIG. 18 is a cutaway view of a human heart illustrating chordae tendineae 28 and papillary muscles 29 in the left 4 and right 6 ventricles. The papillary muscles 29 in the left ventricle 4 attach to the cusps of the mitral valve 22 and the papillary muscles 29 in the right ventricle 6 attach to the cusps of the tricuspid valve 30 via the chordae tendineae 28. FIG. 19 is an isolated view showing attachment of the papillary muscles 29 to the anterior leaflet 26 and posterior leaflet 27 of the mitral valve 22 via chordae tendineae 28. The papillary muscles 29 contract to prevent inversion or prolapse of the mitral valve leaflets 26, 27 (likewise, to prevent inversion or prolapse of the tricuspid valve leaflets by 29, 28 in the right ventricle) during systole (or ventricular contraction). The papillary muscles 29 of both the right 6 and left 4 ventricles begin to contract shortly before ventricular systole and maintain tension throughout. In the case of a normal heart 3 and heart valves, this prevents regurgitation, backward flow of ventricular blood into the atrial cavities, by bracing the atrioventricular valves against prolapse (prolapse described by being forced back into the atria by the high pressure in the ventricles).

However, in some cases of mitral and/or tricuspid regurgitation, the papillary muscles 29 and/or chordae tendineae may apply too much contraction against the valve leaflets, either due to shortening of the chordae tendineae 28/papillary muscles 29 compared to normal, or other reason. In these instances, reduction and or prevention of regurgitation may be helped or accomplished reducing the amount of contraction or force applied through the chordae tendineae 28. Attachment of extension 385 to foundation 285 under tension can draw up the foundation 285 somewhat toward the posterior segment 164, thereby somewhat shortening the distance therebetween, causing a relative reduction in tension on the chordae tendineae 28, which, as a result will allow better closure of the mitral valve leaflets 26,27 during systole, thereby reducing or eliminating mitral valve regurgitation. In combination with the reshaping accomplished by forces applied to the mitral valve annulus 22A (e.g., see FIG. 8) by the anterior and posterior segments 162, 164, the forces applied to the ventricle 4 to reduce tension on the chordae tendineae 28 may cooperate to reduce or eliminate mitral regurgitation. It is further noted that the device 10' could be adapted for similar functioning to reduce or eliminate tricuspid regurgitation from the right ventricle 6 through the tricuspid valve 30.

Figure 20:
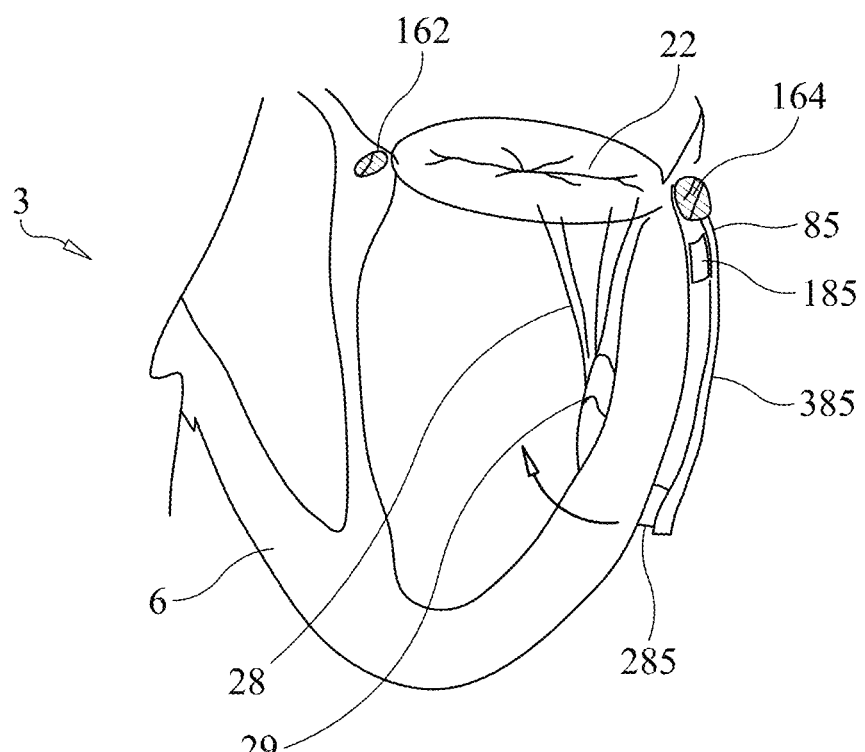
FIG. 20 is a partial, sectional view of a heart illustrating the device of FIG. 16A having been epicardially installed thereon for treatment of mitral valve regurgitation, according to an embodiment of the present invention.

FIG. 20 is a partial, sectional view of a heart 3 on which device 10A is epicardially installed for treatment of mitral valve regurgitation, according to an embodiment of the present invention. The device 10A when properly positioned, applies forces to the valve annulus via at least segments 162, 164. As shown, flap 85 is attached to foundation 185 to maintain the desired position and orientation of the posterior segment 164, while anterior segment is maintained in the desired position in the transverse sinus. Extension(s) 385 extends inferiorly from the flap 85 and is attached to foundation 285 which has been anchored over or inferior of an epicardial location of the ventricle 4 that is apposite to one or more locations of insertion of chordae tendineae 28/papillary muscle 29 into the inner wall of the ventricle 4. After installation of the device 10A as shown, manual adjustments can be made to change the position/orientation of posterior segment 164 as described above. Additionally or alternatively, extension(s) 385 can be manually adjusted to change the amount of tension thereon by detaching extension 385 from foundation 285 and reattaching to shorten or lengthen the distance between the foundation 285 and the posterior segment 164 or flap 85. Adjustment of one or more extensions as described may therefore cause a consequent reduction in tension on the chordae tendineae 28, which, as a result may allow better closure of the mitral valve leaflets 26,27 during systole, thereby reducing or eliminating mitral regurgitation.

Figure 21:
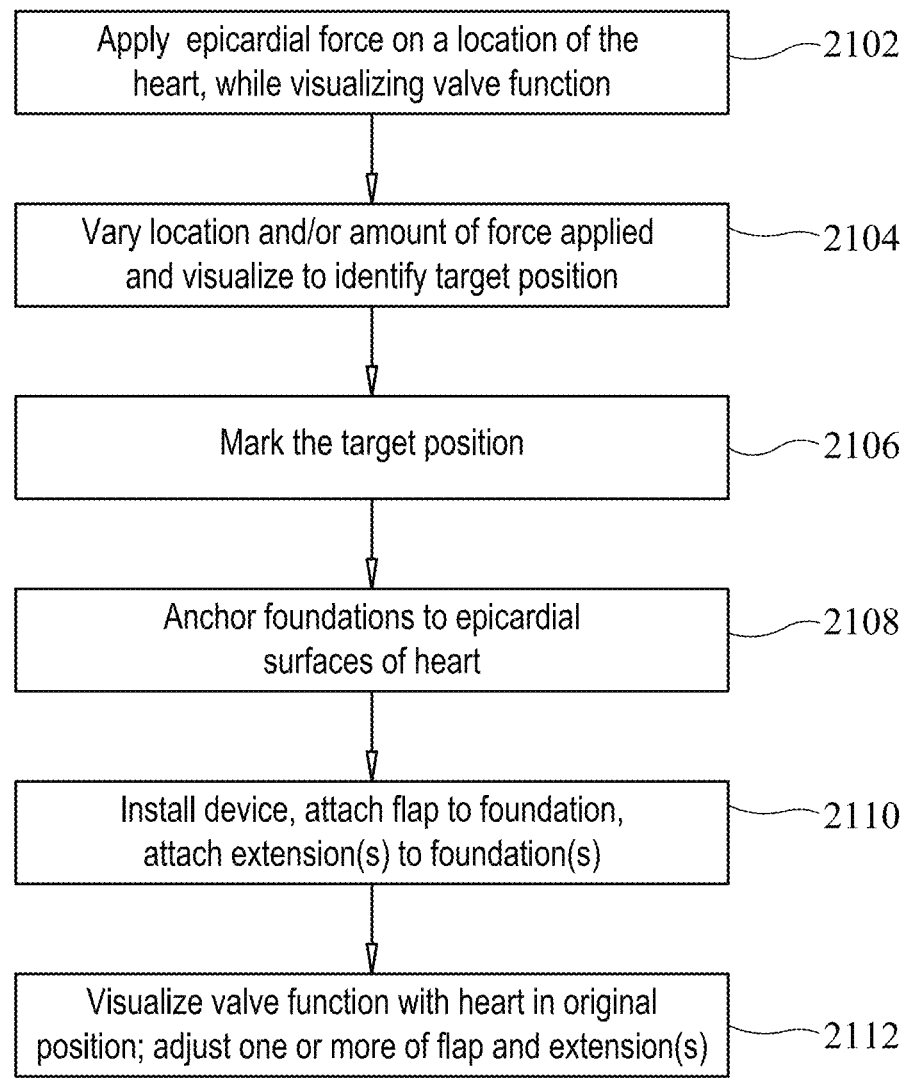
FIG. 21 illustrates a number of events that can be carried out in a method of implanting a device according to an embodiment of the present invention.

FIG. 21 illustrates a number of events that can be carried out in a method of implanting a device according to an embodiment of the present invention. After establishing an opening in the patient to provide access to the heart (which can be open-chest, a lateral thoracotomy, or endoscopic, as noted above, or other opening allowing access), an epicardial force is applied on a location of the heart, while visualizing regurgitation through the valve via visualization apparatus at event 2102. As noted above the force is typically applied to a posterior location of the heart adjacent the valve to be treated. The location of the application of force and/or the amount of force applied can be varied, while continuing the visualization, at event 2104, until a combination of a location and amount of applied force is found where visualization confirms that valve regurgitation is reduced, minimized or eliminated to the satisfaction of the surgeon. The location of the application of force where it is found that the valve regurgitation is reduced, minimized or eliminated as described is considered to be the target location for application of force by a device to be implanted/installed, and the target position is marked at event 2106 according to any of the marking methods previously described.

At event 2108, foundation 185 is anchored to the epicardial surface of the heart to provide a base for fixing an epicardial device thereto. The foundation 185 is fixed according to a predetermined relationship to the marked location so that attachment of the flap 85 to the foundation 185 will result in the posterior segment of the device being located at the target location. Additionally, one or more foundations 285 are anchored to the epicardial surface of the heart 3 at a predetermined distance inferior to the target location. This predetermined distance will have been predetermined to define location(s) that are generally apposite to (or slightly inferior or superior to a location apposite to) one or more locations of insertion of chordae tendineae 28/papillary muscle 29 into the inner wall of the ventricle 4. In a preferred embodiment employing an open chest procedure, the heart 3 is lifted so as to partially extend out of the chest cavity so that the surgeon can directly see the locations on the posterior wall of the heart where the foundations 185 and 285 are to be anchored, and the anchoring is performed with the heart 3 in this position.

At event 2110, the device 10A is installed by inserting the anterior segment 164 in the transverse sinus as described above and contacting the posterior segment 164 to the posterior epicardial surface of the heart 3 at the target location. This location is fixed by attaching flap 85 to the foundation 185. Additionally, extension(s) 385 is/are attached to foundation(s) 285.

To confirm that the device 10 has been properly placed for performance as desired, further visualization of the functioning of the valve may be carried out after the attachment event of 1310. In an open chest procedure, the heart is returned to its original position where the posterior surface of the heart is no longer directly viewable by the surgeon and visualization such as echocardiography is performed to check the degree of regurgitation, if any, that is occurring. If it is seen that a greater amount of regurgitation is occurring than what was occurring during visualization at the time that the target location was identified, then the surgeon may choose to detach the flap 85 from the foundation, reposition the epicardial device 10 to reduce the amount of regurgitation and verify reduction in regurgitation by further visualizing. The flap 85 is reattached to the foundation 185 and further verification can be performed using the visualization. Additionally or alternatively, one or more extensions 385 may be detached from respective foundations 285 and reattached so as to increase or decrease the amount of tension applied by the extension(s) 385. Visualization is again performed to note any change in regurgitation resulting from such adjustments. The events of FIG. 2112 can be repeated as many times as needed until visualization confirms the adjustment levels of the flap 85 and/or extension(s) 385 that provide satisfactory performance in the reduction or elimination of regurgitation.

Further optionally, it may be desirable to perform a length measuring procedure to establish an optimum length or length range for the length 162L of the anterior segment 162 of the device/clip 10 that is to be used for the procedure.

Figure 22:
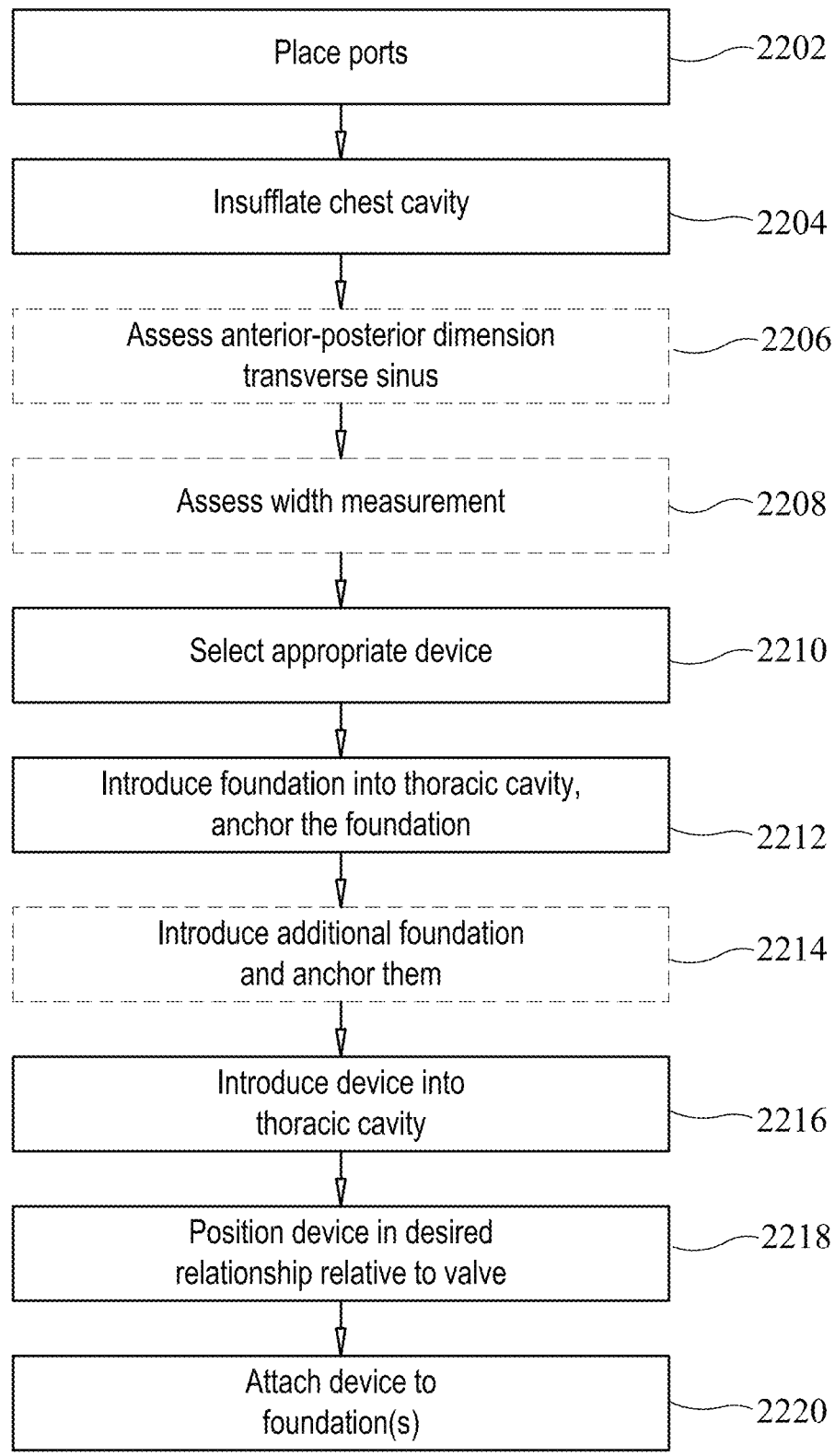
FIG. 22 illustrates events that may be carried out in the performance of a minimally invasive procedure for epicardial implantation of a device for treatment of valve regurgitation according to an embodiment of the present invention.

FIG. 22 illustrates events that may be carried out in the performance of a minimally invasive procedure for epicardial implantation of a device for treatment of valve regurgitation according to an embodiment of the present invention. Although this embodiment is specifically directed to a procedure for treatment of mitral valve regurgitation, it can be readily adapted to similar procedures for treatment of other valves, such as the tricuspid valve, aortic valve or pulmonary valve for example.

Figure 23:
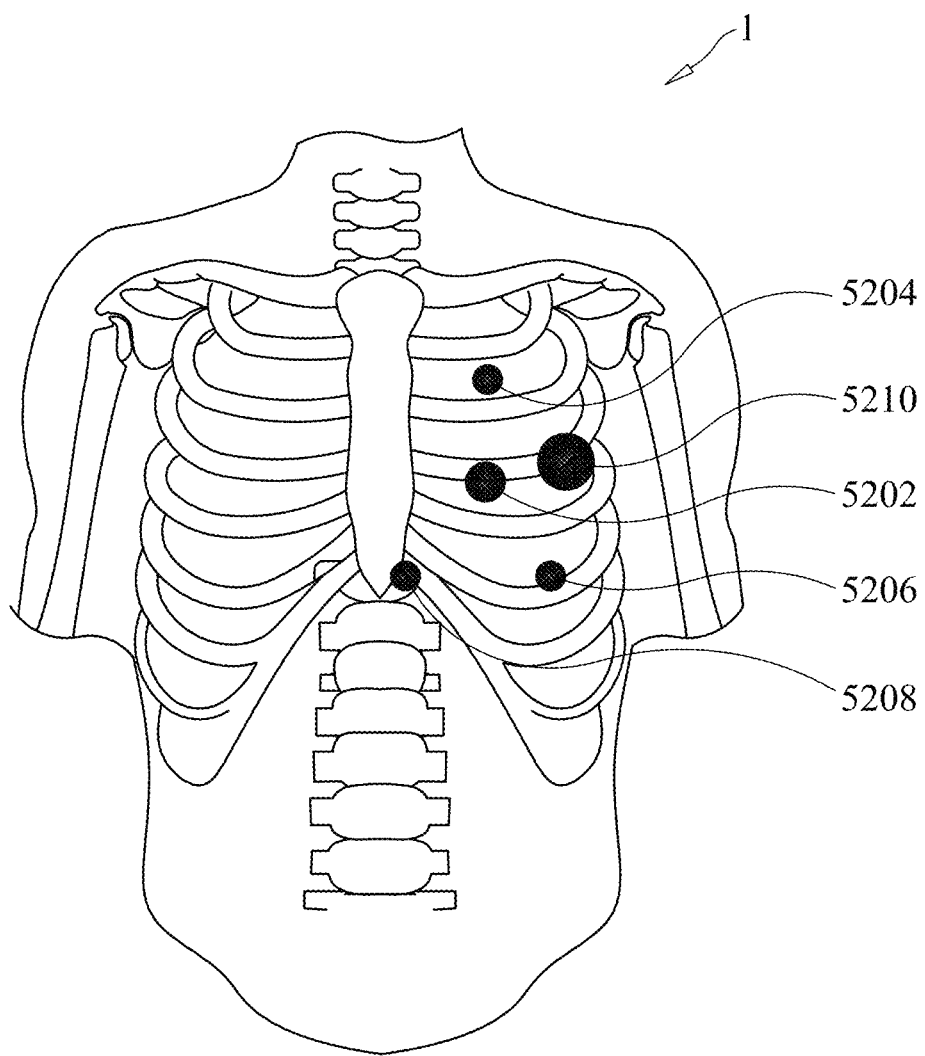
FIG. 23 illustrates locations of port placement in a patient for a procedure according to an embodiment of the present invention.

At event 2202, ports are placed and trocars may be installed for facilitating the procedures that follow. FIG. 23 illustrates locations of port placement in a patient 1 according to one embodiment of the present invention. The port locations and number of ports are not to be considered limiting to the present invention, as the number and locations of the ports may vary and may be a lesser or greater number than the number of ports shown in FIG. 23. In the embodiment shown in FIG. 23, a camera port 5202, which may be a size 8 port may be placed in the $4^{th}$ intercostal space, midclavicular line for use in inserting a camera such as an endoscope therethrough and into the chest cavity of the patient 1. A superior tool port 5204, which may be a size 6 port, may be placed in the $2^{nd}$ intercostal space. An inferolateral tool port 5206, which may be a size 6 port, may be placed in the $6^{th}$ intercostal space, midaxillary line. An inferomedial tool port 5208, which may be a size 6 port, may be placed subxyphoid, and a device placement port 5210, which is sufficiently large to allow device 10 of FIG. 1A (or other device, such as a device for treatment of the tricuspid valve, for example) to pass therethrough, may be placed in the $4^{th}$ intercostal space, midaxillary line. In a preferred embodiment, the device placement port 5210 may be an Alexis O Wound Protector/Retractor, available from Applied Medical. However, other ports having sufficient size and similar features may be substituted. Furthermore a smaller port 5210 may be used when the implantation procedure uses a device having separate segments that can be assembled after they have been passed through the port and into the chest cavity, like that disclosed in International Application Serial No. PCT/US2019/015300, which has been incorporated herein, in its entirety, by reference thereto above.

At event 2204 the chest cavity of the patient 1 is insufflated and surgical tools and camera/endoscope may be placed through the appropriate ports. Insufflation may be to a pressure in a range of ten to fifteen atmospheres, for example. The pericardium is accessed and opened sufficiently to allow placement of the device 10 (or alternatively, another device as described herein or in any of the applications which have been incorporated by reference herein). Optionally, event 5106 may be carried out to assess the anterior posterior dimension (usable length) of the transverse sinus 14, in order to provide a length measurement for the anterior segment 162 of a device to be implanted, as described in detail above. A length sizing instrument 600 can be inserted through one of the tool ports such as 5204 using graspers and manipulated via the graspers to insert it into the transverse sinus for measurement thereof. Using a robotic arm, the sizing tool 600 is grasped at its anterior dimension where it joins the end of the transverse sinus 14 and then the tool is withdrawn from the transverse sinus. The camera can be used not only for the procedures described previously, but also to read the anterior-posterior dimension, or length where the robotic arm grasps the tool 600 as indicated by gradations 604. The sizing tool 600 can then be withdrawn from the chest cavity using the graspers.

Optionally, a width measurement may be performed at event 2208 to assess a width 160 to use for selecting a device that has a width 160 that most closely matches the measurement. To perform this assessment, a width measuring instrument 500 may be placed through the device port 5210 and positioned and manipulated using graspers or a handle 550 or 560 as disclosed in International Application Serial No. PCT/US2019/015300. Forces are applied by the instrument 500, with repositioning as necessary, while visualizing the mitral valve as described previously to determine when the instrument 500 is positioned in the best location and with the best force applied for minimizing or eliminating mitral valve regurgitation. The width measurement can be made at this time using the same visualization techniques described above. After the width measurement has been determined, the instrument 500 can be removed from the chest cavity through the device port 5210. It is noted that a similar procedure can be carried out with regard to the tricuspid valve to measure a width of a device to be used in treatment of the tricuspid valve.

At event 2210, a device is selected for implantation if it has not already been selected (such as in instances where 2206 and 2208 are not performed and the device is preselected, for example). In instances where one or both of the optional events 5106, 5108 are carried out, the device can be selected to have an optimum anterior segment 162 length and/or distance 160D from various devices that are available for selection and which have varying anterior segment lengths and distances 160D. At event 2212, the foundation 185 is introduced into the thoracic cavity by passing it through one of the ports (e.g., device port 5210) using graspers or other tool configured for operation from outside the port. Foundation 185 may be anchored to the epicardial surface of the heart to provide a base for fixing the epicardial device thereto. The foundation 185 is fixed according to a predetermined relationship to a target location where the device is to be positioned to apply optimum forces to the epicardial surface of the heart. In instances where event 2208 has been performed, the foundation is fixed at a location having a predetermined locational relationship to the marked location where the device is to apply force, so that attachment of the flap 85 to the foundation 185 will result in the posterior segment of the device being located at the target location. Optionally, one or more foundations 285 may be introduce into the chest cavity at optional event 2214 through one or more of the ports and may be anchored to the epicardial surface of the heart 3 at a predetermined distance inferior to the target location. This predetermined distance will have been predetermined to define location(s) that are generally apposite to (or slightly inferior or superior to a location apposite to) one or more locations of insertion of chordae tendineae 28/papillary muscle 29 into the inner wall of the ventricle 4 (or ventricle 6 if procedure is for tricuspid valve). The foundation 185, as well as the foundations 285, when optionally used, may be anchored to the epicardial wall of the heart 3 using tacks, helical screws, or other fixator, preferably of a type that allows removal in instances where the foundation needs to be removed or replaced. A fixator driver as described in International Application Serial No. PCT/US2019/015300 may be used to install the fixators through the foundation(s) to anchor it to the epicardial wall.

At event 2216 the selected device may be introduced into the thoracic cavity through the device port 5210, using an implant insertion cradle described in International Application Serial No. PCT/US2019/015300, graspers, forceps and or other instruments suitable for use in an endoscopic procedure. The device port 5210 may be sealed with wetted gauze at the time of placement. If a width sizing procedure is performed (optional event 2208) then the wetted gauze can be removed at that time. If event 2208 is not performed, or if the wetted gauze was replaced after performing event 2208, then the wetted gauze is removed at this time to open the port 5210 to allow the device to be delivered therethrough. The device is typically angled in orientation to allow it to be passed through the port 5210. For example the device may be angled to insert the anterior segment 162 first. After passing the device through the port 5210, the wetted gauze may be replaced over the port 5210 to help maintain the insufflation pressure.

At event 2218 the device is manipulated via graspers, forceps and/or insertion cradle to position the device in a desired relationship where it partially surrounds the valve being treated and may be in, near or intersecting a plane of the valve, In a case where the valve being treated in the mitral valve, the anterior segment 162 of the device 10 may be inserted into the transverse sinus 14. Visualization via the camera can be used to ensure that force on the transverse sinus 14 is directed toward the lateral wall. Optionally, transesophageal echocardiography (TEE) may be used to evaluate the left ventricle dimensions and ensure that left atrial perforation does not occur. At event 2220 the device is attached to the foundation 185 and, optionally, one or more foundations 285, thereby anchoring the device in a desired position and orientation relative to the heart and the heart valve that it is treating.

After completion of the implantation procedure or completion of removal of the device, all instruments/tools are removed, insufflation is ceased, the ports are removed, and the patient is closed according to standard procedures to complete the surgical procedure.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

For example, any of the methods described herein can be practiced with other devices such as those described in any of the applications and provisional applications that have incorporated by reference herein, in their entireties. Thus, in addition or alternative to adjusting a device using flap 85 and flap and/or flap 385, a device as described in Application Ser. No. 62/622,831 may be used and manual adjustment of the device 10A, 10B or 10C in any of the manners described therein may be used to additionally or alternatively make adjustments to the forces applied by the device. Likewise in addition or alternative to adjusting a device using flap 85 and flap and/or flap 385, a device as described in Application Ser. No. 62/622,827 may be used and automatic adjustment of the device in any of the manners described therein may be used to additionally or alternatively make adjustments to the forces applied by the device.

That which is claimed is:

1. An epicardial device for reducing or preventing regurgitation of blood through a valve of a heart, said device comprising:
    a main body having a segment adapted to apply force to an epicardial surface of the heart;
    a member that applies counterforce to said force applied by said segment;
    a foundation configured to be anchored to the epicardial surface of the heart, said foundation comprising a surface configured with attachment features; and
    said device further comprising a surface configured with mating attachment features configured to attach to said attachment features of said foundation;
    wherein said mating attachment features and attachment features are separable and reattachable to allow repositioning of at least a portion of said device relative to said foundation.

2. The epicardial device of claim 1, comprising a flap extending from said segment, said flap comprising a mating surface configured with said mating attachment features.

3. The epicardial device of claim 1,
    wherein said segment comprises a rigid structural rib contained within a pad;
    wherein said pad comprises a contact surface configured to apply said force to the epicardial surface.

4. The epicardial device of claim 2,
    wherein said segment comprises a pad;
    wherein said pad comprises a contact surface configured to apply said force to the epicardial surface; and
    wherein said flap extends inferiorly from said pad.

5. The epicardial device of claim 4, wherein said pad is configured to apply force to a posterior surface of the heart at a location superior to a location where said foundation is configured to be anchored.

6. The epicardial device of claim 4, wherein a rigid structural rib is contained within said pad.

7. The epicardial device of claim 2, wherein said flap is reattachable to said foundation to change a distance between said foundation and said segment.

8. The epicardial device of claim 1 configured for reshaping an annulus of a mitral valve of the heart.

9. The epicardial device of claim 1 configured for reshaping one or more dimensions of a left ventricle of the heart.

10. The epicardial device of claim 1 configured for reshaping an annulus of a tricuspid valve of the heart.

11. The epicardial device of claim 1 configured for reshaping one or more dimensions of a right ventricle of the heart.

12. The epicardial device of claim 1, wherein
    said segment comprises a posterior segment adapted to be contacted to a posterior surface of the heart, said member comprises an anterior segment configured to be contacted to an anterior surface of the heart, and said main body further comprises a lateral segment joining said anterior segment and said posterior segment.

13. The epicardial device of claim 12, wherein an annulus of a mitral valve lies in a plane between a left atrium and a left ventricle of the heart, the anatomy of the heart includes an aorta, a pulmonary trunk, a superior vena cava, a transverse sinus, an oblique sinus, and an atrioventricular groove;
    wherein said anterior segment is configured to be positioned in the transverse sinus of the heart;
    wherein said posterior segment is configured to be positioned on or inferior to the atrioventricular groove of the heart; and
    wherein said lateral segment extends between said anterior segment and said posterior segment.

14. The epicardial device of claim 1, wherein said foundation comprises a first foundation, said epicardial device further comprising a second foundation, wherein said second foundation is configured to be anchored to the epicardial surface of the heart at a location inferior to a location where said first foundation is configured to be anchored;
    said second foundation comprising a second surface configured with second attachment features; and
    said device further comprising a surface configured with second mating attachment features configured to attach to said second attachment features of said second foundation;
    wherein said second mating attachment features and second attachment features are separable and reattachable to allow repositioning of at least a second portion of said device relative to said second foundation.

15. The epicardial device of claim 14, comprising a flap extending from said segment and an extension extending from one of said segment or said flap;
    wherein said extension is reattachable to said second foundation to change a distance between said second foundation and said first foundation.

16. The epicardial device of claim 14, further comprising a third foundation, wherein said third foundation is configured to be anchored to the epicardial surface of the heart at a location inferior to a location where said first foundation is configured to be anchored and separate from a location where said second foundation is configured to be anchored;
    said third foundation comprising a third surface configured with third attachment features; and
    said device further comprising a surface configured with third mating attachment features configured to attach to said third attachment features of said third foundation;
    wherein said third mating attachment features and third attachment features are separable and reattachable to allow repositioning of at least a third portion of said device relative to said third foundation.

17. The epicardial device of claim 16, comprising a flap extending from said segment and a first extension extending from one of said segment or said flap; and a second extension extending from one of said segment or said flap;

wherein said first extension is reattachable to said second foundation to change a distance between said second foundation and said first foundation; and wherein said second extension is reattachable to said third foundation to change a distance between said third foundation and said first foundation.

18. An epicardial device for placement on the epicardial surface of a heart in order to reshape the annulus of the mitral valve of the heart, the mitral valve lying in a plane between the left atrium and the left ventricle of the heart, the anatomy of the heart includes an aorta, a pulmonary trunk, a superior vena cava, a transverse sinus, and an atrioventricular groove, the epicardial device comprising:

an anterior segment, a posterior segment and a lateral segment extending between the anterior segment and the posterior segment;

wherein the anterior segment is configured and dimensioned to at least partially occupy the transverse sinus epicardially;

wherein the lateral segment is configured for positioning the anterior segment on or above a plane in which the mitral valve is located, and the posterior segment on or below the plane in which the mitral valve is located, and below a position of the anterior segment;

wherein the posterior segment is configured to apply a force to a posterior epicardial surface of the heart;

a foundation configured to be anchored to the posterior epicardial surface of the heart, said foundation comprising a surface configured with attachment features; and said device further comprising a surface configured with mating attachment features configured to attach to said attachment features of said foundation;

wherein said mating attachment features and attachment features are separable and reattachable to allow repositioning of at least said posterior segment relative to said foundation.

19. The epicardial device of claim 18, comprising a flap extending from said posterior segment, said flap comprising a mating surface configured with said mating attachment features, wherein said flap is attachable, detachable and reattachable to and from said foundation to affect a change in position of at least said posterior segment relative to said foundation when said foundation is anchored.

20. The epicardial device of claim 19, wherein said foundation comprises a first foundation, said epicardial device further comprising a second foundation, wherein said second foundation is configured to be anchored to the epicardial surface of the heart at a location inferior to a location where said first foundation is configured to be anchored;

said second foundation comprising a second surface configured with second attachment features; and said device further comprising a surface configured with second mating attachment features configured to attach to said second attachment features of said second foundation;

wherein said second mating attachment features and second attachment features are separable and reattachable to allow repositioning of at least a second portion of said device relative to said second foundation.

21. The epicardial device of claim 19, comprising a flap extending from said segment and an extension extending from one of said posterior segment or said flap;

wherein said second foundation is configured to be attached to the epicardial surface of the heart;

wherein said extension is reattachable to said second foundation to apply forces to the epicardial surface to reduce tension on chordae tendineae of the heart.

22. The epicardial device of claim 20, further comprising a third foundation, wherein said third foundation is configured to be anchored to the epicardial surface of the heart at a location inferior to a location where said first foundation is configured to be anchored and separate from a location where said second foundation is configured to be anchored;

said third foundation comprising a third surface configured with third attachment features; and said device further comprising a surface configured with third mating attachment features configured to attach to said third attachment features of said third foundation;

wherein said third mating attachment features and third attachment features are separable and reattachable to change force applied between said third foundation and said posterior segment.

23. A method of epicardial treatment of valve regurgitation associated with a valve of a heart of a patient, the method comprising:

establishing at least one opening in the patient to provide access to the heart;

applying an epicardial force on a location of the heart, while visualizing regurgitation through the valve via visualization apparatus;

varying at least one of the location or the amount of epicardial force applied to identify a target position where valve regurgitation is reduced or eliminated;

marking the target position;

anchoring a foundation to the epicardial surface of the heart to provide a base for fixing an epicardial device thereto; and fixing the epicardial device to the foundation, wherein said fixing establishes a segment of said device in the target position and wherein said fixing indirectly fixes the epicardial device to the heart.

24. The method of claim 23, comprising further visualizing functioning of the valve after said fixing the epicardial device;

detaching the epicardial device from the foundation when said further visualizing shows an unacceptable amount of regurgitation;

repositioning the epicardial device to reduce the amount of regurgitation and verifying reduction in regurgitation by said further visualizing; and re-attaching the epicardial device to the foundation.

25. The method of claim 23, wherein the foundation comprises a first foundation, said method further comprising:

anchoring a second foundation to the epicardial surface of the heart; and attaching an extension between the second foundation and one of the first foundation or the segment to apply compression forces between the second foundation and the one of the first foundation or the segment to reduce tension on chordae tendineae of the heart.

26. The method of claim 23, wherein the valve is the mitral valve, the segment comprises a posterior segment, the epicardial device further comprises an anterior segment, an anterior end, a posterior end and a lateral segment extending between the anterior segment and the posterior segment;

wherein the anterior and posterior segments are positioned epicardially on the heart at locations apposite to an annulus of the mitral valve, such that the anterior and posterior segments apply force sufficient to reshape the annulus.

27. The method of claim 23, further comprising:
measuring a distance between opposing epicardial surfaces of the heart where one of the opposing epicardial surfaces is measured at the target position; and
selecting the epicardial device so that the epicardial device is configured with opposed force applying segments separated by a distance that approximates the measured distance between the opposing epicardial surfaces, when said epicardial device is installed on the heart and fixed to the foundation.

28. The method of claim 26, further comprising:
measuring an unobstructed length of a transverse sinus of the heart; and
providing the epicardial device to have an anterior segment length less than or equal to the unobstructed length, wherein the anterior segment is positioned in the transverse sinus prior to said fixing.

29. A method of epicardial treatment of mitral valve regurgitation associated with a mitral valve of a heart of a patient, the anatomy of the heart including an aorta, a pulmonary trunk, a superior vena cava, a transverse sinus, a left atrial appendage, and an oblique sinus, the method comprising:
applying an epicardial force on a posterior location of the heart, while visualizing regurgitation through the valve via visualization apparatus;
varying at least one of the location or the amount of epicardial force applied to identify a target position where mitral valve regurgitation is reduced or eliminated;
marking the target position;
anchoring a foundation to the epicardial surface of the heart at a location having a predefined relationship to the marking;
providing a clip having an anterior segment, an anterior end, a posterior segment, a posterior end and a lateral segment extending between the anterior segment and the posterior segment;
positioning the anterior and posterior segments epicardially on the heart at locations apposite to an annulus of the mitral valve, such that the anterior and posterior segments apply force sufficient to reshape the annulus, wherein the posterior segment is located on the target position;
fixing the clip to the foundation, wherein said fixing maintains the posterior segment in the target position.

30. The method of claim 29, wherein the anterior segment is at least partially inserted into a transverse sinus of the heart and the transverse sinus maintains a position of said anterior segment.

31. The method of claim 29, further comprising:
detaching the clip from the foundation to allow repositioning the clip to reduce an amount of mitral regurgitation;
repositioning the clip to reduce the amount of regurgitation and verifying reduction in regurgitation by further visualizing; and
re-attaching the clip to the foundation.

32. The method of claim 29, further comprising:
anchoring a second foundation to the epicardial surface of the heart at a second location;
attaching an extension to said second foundation, said extension extending from one of said foundation or said clip, to establish a compression force between said second foundation and said one of said foundation or said clip, to reduce tension on chordae tendineae of the heart.

33. The method of claim 32, further comprising:
detaching the extension from the second foundation; and
re-attaching the extension to the second foundation in a relative position to vary the amount of reduction in tension on the chordae tendineae.

34. A minimally invasive method for epicardial implantation of a device for treatment of valve regurgitation, said method comprising:
installing a device port, a camera port and at least one instrument port in the chest of a patient to permit access to a chest cavity of the patient by the device, a camera and instruments;
insufflating the chest cavity;
positioning the camera though the camera port and into the chest cavity;
introducing a foundation through one of the ports;
anchoring the foundation to an epicardial surface of the heart;
introducing the device through the device port and into the chest cavity using an instrument controlled from outside the chest cavity and device port;
manipulating the device to partially surround an annulus of a valve by placement of the device on epicardial walls of the heart at locations that partially surround the annulus; and
anchoring the device to the epicardial walls of the heart at least in part by attaching a portion of the device to the anchored foundation.

* * * * *